United States Patent
Stiles et al.

(12)

(10) Patent No.: US 6,448,474 B1
(45) Date of Patent: *Sep. 10, 2002

(54) PURIFIED PROTEINS, RECOMBINANT DNA SEQUENCES AND PROCESSES FOR CONTROLLING THE RIPENING OF COFFEE PLANTS

(75) Inventors: John I. Stiles, Kaneohe; Istefo Moisyadi; Kabi Raj Neupane, both of Honolulu, all of HI (US)

(73) Assignee: University of Hawaii, Honolulu, HI (US)

(*) Notice: Subject to any disclaimer, the term of this patent is extended or adjusted under 35 U.S.C. 154(b) by 0 days.

This patent is subject to a terminal disclaimer.

(21) Appl. No.: 09/255,154

(22) Filed: Feb. 22, 1999

Related U.S. Application Data

(63) Continuation-in-part of application No. 08/695,412, filed on Aug. 12, 1996, now Pat. No. 5,874,269, which is a continuation-in-part of application No. 08/485,107, filed on Jun. 7, 1995, now Pat. No. 5,767,376.

(51) Int. Cl.[7] ......................... C12N 15/09; C12N 15/29; C12N 15/82; A01H 5/00; A01H 5/08

(52) U.S. Cl. ..................... 800/283; 800/278; 800/285; 800/286; 800/287; 800/298; 435/419; 435/468; 435/320.1; 435/183; 435/189; 536/23.2; 536/23.6; 536/24.1; 536/24.5

(58) Field of Search .................... 800/278, 287, 800/286, 283, 285, 298; 435/419, 468, 320.1, 183, 189; 536/23.2, 23.6, 24.1, 24.5

(56) References Cited

U.S. PATENT DOCUMENTS

| | | | |
|---|---|---|---|
| 5,304,490 A | 4/1994 | Bird et al. | 435/320.1 |
| 5,334,529 A | 8/1994 | Adams et al. | 435/418 |
| 5,356,799 A | 10/1994 | Fabijanski et al. | 800/274 |
| 5,364,780 A | 11/1994 | Hershey et al. | 800/294 |
| 5,365,015 A | 11/1994 | Grierson et al. | 800/283 |
| 5,367,065 A | 11/1994 | Ecker et al. | 536/23.6 |
| 5,416,250 A | 5/1995 | Ferro et al. | 800/283 |
| 5,436,395 A | 7/1995 | Sondahl et al. | 800/298 |
| 5,444,166 A | 8/1995 | Ecker et al. | 536/23.6 |
| 5,449,764 A | 9/1995 | Bird et al. | 536/23.2 |
| 5,451,514 A | 9/1995 | Boudet et al. | 800/286 |
| 5,453,566 A | 9/1995 | Shewmaker et al. | 800/286 |
| 5,457,041 A | 10/1995 | Ginavan et al. | 435/455 |
| 5,530,190 A | 6/1996 | Grierson et al. | 800/283 |
| 5,702,933 A | 12/1997 | Klee et al. | 435/172.3 |
| 5,723,766 A | 3/1998 | Theologis et al. | 800/205 |
| 5,767,376 A | 6/1998 | Stiles et al. | 536/23.6 |

FOREIGN PATENT DOCUMENTS

| | | |
|---|---|---|
| EP | 0 240 208 | 3/1987 |
| WO | WO 91/01375 | 2/1991 |
| WO | WO 92/04456 | 3/1992 |
| WO | WO 95/33377 | 12/1995 |
| WO | WO 96/07742 | 3/1996 |
| WO | WO 96/19103 | 6/1996 |
| WO | WO 96/21027 | 7/1996 |
| WO | WO 98/06852 | 2/1998 |

OTHER PUBLICATIONS

Theologis, A. et al. (1993) Modifying fruit ripening by suppressing gene expression. Cellular & molecular aspects of the plant hormone ethylene. Ed. Pech et al., Klyver Academic Pub., pp. 19–23.

Theologis, A. (1992). One rotten apple spoils the whole bushel: The Role of Ethylene in Fruit Ripening. *Cell* 70, 181–184.

Oeller, P.W. (1991). Reversible inhibition of tomato fruit sensescence by antisense RNA. *Science*, pp. 437–439, Oct. 1991.

Smith et al, "Antisense RNA inhibition of polygalacturonase gene expression in transgenic tomatoes", 1988, Nature vol. 334 No. 5 pp. 724–726.*

Napoli, "Introduction of a Chimeric Chalcone Synthase Gene into Petunia Results in Reversible Co–Suppression of Homologous Genes in trans", Apr. 1990, The Pant Cell vol. 2, pp. 279–289.*

Smith, C.J.S. et al. Antisense RNA inhibition of polygalacturonase gene expression in transgenic tomatoes, *Nature* 334: 724–726, 1988.

Theologis, A. et al.(1993). Use of a tomato mutant constructed with reverse genetics to study fruit ripening, a complex developmental process. Developmental Genetics, vol. 14, p. 285–295 (abstract only).

(List continued on next page.)

*Primary Examiner*—David T. Fox
*Assistant Examiner*—Medina A. Ibrahim
(74) *Attorney, Agent, or Firm*—Jones, Day, Reavis & Pogue

(57) ABSTRACT

The invention establishes that coffee fruit ripening is climacteric. The invention further provides techniques to isolate substantially pure RNA from coffee fruit even though the fruit contains high levels of phenolic compounds and carbohydrate which would otherwise interfere with obtaining clean RNA preparations from this tissue. The invention provides purified proteins, nucleic acid sequences that code on expression therefore and recombinant DNA molecules, including hosts transformed therewith, and methods for transforming coffee plants to suppress the expression of coffee fruit-expressed ACC synthase and/or coffee fruit-expressed ACC oxidase necessary for ethylene biosynthesis and the ripening of coffee fruit. Coffee plants are transformed with vectors containing coffee fruit-expressed ACC synthase and/or with ACC oxidase DNA sequences that code on expression for the respective RNA that is antisense or sense to the mRNA for the respective ACC synthase and/or ACC oxidase. The result is that the expression of the respective enzyme is eliminated and the transformed plants are incapable of synthesizing ethylene during coffee fruit ripening, although other aspects of their metabolism is not affected. The invention further provides methods for controlling the ripening of coffee fruit from the transformed coffee plants by applying exogenous ethylene.

32 Claims, 17 Drawing Sheets

OTHER PUBLICATIONS

Schuch, U.K. et al. (1992). Flowering, ethylene production, and ion leakage of coffee in response to water stress and gibberellic acid. *Journal of the American Society for Horticultural Science* 177, 158–163.

Nagata, M. et al. (1995) Modification of tomato fruit ripening by transformation with sense or antisense chimeric 1–aminocyclopropane–1–carboxylate synthase genes. *Acta Horticulture*, No. 394, 213–218 (abstract only).

Spiral, J. and V. Petiard (1993). Development of a transformation method for coffee and regeneration of transgenic coffee plantlets. *Colloq. Sci. Int. Cafe*, 15, 115–122. (abstract only).

Clifford, M.N. & J.R. Ramirez–Martinez (1991). Phenols and caffeine in wet–processed coffee beans and coffee pulp. *Food Chemistry* 40, 35–42. (abstract only).

Budiani, A. (1989). Extraction of protein and esterase isoenzymes from coffee leaves. *Menara Perkebunan* 57, 94–98. (abstract only).

Bicchi, C.P. et al. (1995). Characterization of green and roasted coffees through the chlorogenic acid fraction by HPLC–UV and principal component analysis. *Journal of agricultural and food chemistry* 43, 1549–1555.

Aerts R.J. and T.W. Baumann (1994). Distribution and utilization of chlorogenic acid in *Coffea* seedlings. *Journal of Experimental Botany* 45, 497–503.

Clifford, M.N. & T. Kazi (1987). The influence of coffee bean maturity on the content of chlorogenic acids, caffeine and trigeonelline. *Food Chemistry* 26, 59–69.

Ramirez–Martinez, J.R. & M.N. Clifford (1989). Phenolic acids in coffee pulp. Association Scientifique du Cafe, 13th International scientific colloquium on coffee, Paipa (Colmbia) Aug. 21–25, 1989. (French).

Ramirez–Martinez, J.R. (1988). Phenolic compounds in coffee pulp: quantitative determination by HPLC. *J. Sci. Food Agric.* 43, 135–144.

Fourney, R.M. et al. (1988). Northern blotting: Efficient RNA staining and transfer. *Focus* 10, 507.

Levi, A. et al., (1992). A rapid procedure for the isolation of RNA from high–phenolic–containing tissues of pecan. *HortScience* 27, 1316–1318.

Lincoln, J.E. et al. (1993). LE–ACS4, a fruit ripening and wound–induced 1–aminocyclopropane–1–carboxylate synthase gene of tomato (*Lycopersicon esculentum*). *The Journal of Biological Chemistry* 268, 19422–19430.

Suzuki, T. et al. (1992) Purine and purine alkaloid metabolism in *Camellia* and *Coffea* plants. Review Article No. 68. *Phytochemistry* 31 (8), 2578–2584.

* cited by examiner

FIGURE 1: DEDUCED AMINO ACID SEQUENCE OF ACC SYNTHASE FROM COFFEA ARABICA (SEQ ID NO:10)

```
Met Glu Phe Ser Leu Lys Asn Glu Gln Gln Gln Leu Leu Ser Lys
 1            5                  10                     15

Met Ala Thr Asn Asp Gly His Gly Glu Asn Ser Pro Tyr Phe Asp
               20                  25                     30

Gly Trp Lys Ala Tyr Asp Ser Asp Pro Tyr His Pro Thr Arg Asn
               35                  40                     45

Pro Asn Gly Val Ile Gln Met Gly Leu Ala Glu Asn Gln Leu Cys
               50                  55                     60

Phe Asp Leu Ile Glu Glu Trp Val Leu Asn Asn Pro Glu Ala Ser
               65                  70                     75

Ile Cys Thr Ala Glu Gly Ala Asn Lys Phe Met Glu Val Ala Ile
               80                  85                     90

Tyr Gln Asp Tyr His Gly Leu Pro Glu Phe Arg Asn Ala Val Ala
               95                 100                    105

Arg Phe Met Glu Lys Val Arg Gly Asp Arg Val Lys Phe Asp Pro
              110                 115                    120

Asn Arg Ile Val Met Ser Gly Gly Ala Thr Gly Ala His Glu Thr
              125                 130                    135

Leu Ala Phe Cys Leu Ala Asp Pro Glu Asp Ala Phe Leu Val Pro
              140                 145                    150

Thr Pro Tyr Tyr Pro Gly Phe Asp Arg Asp Leu Arg Trp Arg Thr
              155                 160                    165

Gly Met Gln Leu Leu Pro Ile Val Cys Arg Ser Ser Asn Asp Phe
              170                 175                    180

Lys Val Thr Lys Glu Ser Met Glu Ala Ala Tyr Gln Lys Ala Gln
              185                 190                    195

Glu Ala Asn Ile Arg Val Lys Gly Phe Leu Leu Asn Asn Pro Ser
              200                 205                    210

Asn Pro Leu Gly Thr Val Leu Asp Arg Glu Thr Leu Ile Asp Ile
              215                 220                    225
```

FIGURE 1 (continued)

```
Val Thr Phe Ile Asn Asp Lys Asn Ile His Leu Ile Cys Asp Glu
            230                 235                 240

Ile Tyr Ser Ala Thr Val Phe Ser Gln Pro Glu Phe Ile Ser Ile
            245                 250                 255

Ser Glu Ile Ile Glu His Asp Val Gln Cys Asn Arg Asp Leu Ile
            260                 265                 270

His Leu Val Tyr Ser Leu Ser Lys Asp Leu Gly Phe Pro Gly Phe
            275                 280                 285

Arg Val Gly Ile Leu Tyr Ser Tyr Asn Asp Ala Val Val Ser Cys
            290                 295                 300

Ala Arg Lys Met Ser Ser Phe Gly Leu Val Ser Thr Gln Thr Gln
            305                 310                 315

His Leu Ile Ala Ser Met Leu Ser Asp Glu Ala Phe Met Asp Lys
            320                 325                 330

Ile Ile Ser Thr Ser Ser Glu Arg Leu Ala Ala Arg His Gly Leu
            335                 340                 345

Phe Thr Arg Gly Leu Ala Gln Val Gly Ile Gly Thr Leu Lys Ser
            350                 355                 360

Ser Ala Gly Leu Tyr Phe Trp Met Asp Leu Arg Arg Leu Leu Arg
            365                 370                 375

Glu Ser Thr Phe Glu Ala Glu Met Glu Leu Trp Arg Ile Ile Ile
            380                 385                 390

His Glu Val Lys Leu Asn Val Ser Pro Gly Leu Ser Phe His Cys
            395                 400                 405

Ser Glu Pro Gly Trp Phe Arg Val Cys Phe Ala Asn Met Asp Asp
            410                 415                 420

Glu Ser Val Arg Val Ala Leu Arg Arg Ile His Lys Phe Val Leu
            425                 430                 435

Val Gln Gly Lys Ala Thr Glu Pro Thr Thr Pro Lys Ser Arg Cys
            440                 445                 450
```

FIGURE 1 (continued)

```
Gly Ser Ser Lys Leu Gln Leu Ser Leu Ser Phe Arg Arg Leu Asp
                455                 460                 465

Glu Arg Val Met Gly Ser His Met Met Ser Pro His Ser Pro Met
                470                 475                 480

Ala Ser Pro Leu Val Arg Ala Thr
                485
```

FIGURE 2: COFFEE FRUIT-EXPRESSED ACC SYNTHASE GENE SEQUENCE
(SEQ ID NO:11)

```
GTAATCTCTT CTAAAATCAA CCATTCTCTT CATTCTTCAC TTGACAAGGC      50

CACTGCATTC TTCATTCTTT CTTGATATAT AGCCATTTTT TTCATTCTTT     100

CTTGATATAT AGCCATTTTT TTCATTCTTT CTTCATTCAT TGTCTGGAGA     150

AGTTGGTTGA GTTTTCTTGA AAATTCAAGC AAAACA ATG GAG TTC AGT    198
                                       Met Glu Phe Ser
                                         1

TTG AAA AAC GAA CAA CAA CAA CTC TTG TCG AAG ATG GCA ACC    240
Leu Lys Asn Glu Gln Gln Gln Leu Leu Ser Lys Met Ala Thr
 5                   10                  15

AAC GAT GGA CAT GGC GAA AAC TCG CCT TAT TTT GAT GGT TGG    282
Asn Asp Gly His Gly Glu Asn Ser Pro Tyr Phe Asp Gly Trp
     20                  25                  30

AAG GCA TAT GAT AGT GAT CCT TAC CAT CCC ACC AGA AAT CCT    324
Lys Ala Tyr Asp Ser Asp Pro Tyr His Pro Thr Arg Asn Pro
         35                  40                  45

AAT GGT GTT ATA CAG ATG GGA CTC GCA GAA AAT CAG TTA TGC    366
Asn Gly Val Ile Gln Met Gly Leu Ala Glu Asn Gln Leu Cys
             50                  55                  60

TTT GAT TTG ATC GAG GAA TGG GTT CTG AAC AAT CCA GAG GCT    408
Phe Asp Leu Ile Glu Glu Trp Val Leu Asn Asn Pro Glu Ala
                 65                  70

TCC ATT TGC ACA GCA GAA GGA GCG AAC AAA TTC ATG GAA GTT    450
Ser Ile Cys Thr Ala Glu Gly Ala Asn Lys Phe Met Glu Val
 75                  80                  85

GCT ATC TAT CAA GAT TAT CAT GGC TTG CCA GAG TTC AGA AAT    492
Ala Ile Tyr Gln Asp Tyr His Gly Leu Pro Glu Phe Arg Asn
     90                  95                 100

GCT GTA GCA AGG TTC ATG GAG AAG GTG AGA GGT GAC AGA GTC    534
Ala Val Ala Arg Phe Met Glu Lys Val Arg Gly Asp Arg Val
        105                 110                 115
```

FIGURE 2 (continued)

| | | | | | | | | | | | | |
|---|---|---|---|---|---|---|---|---|---|---|---|---|
| AAG | TTC | GAT | CCC | AAC | CGC | ATT | GTG | ATG | AGT | GGT | GGG | GCA | ACC | 576
| Lys | Phe | Asp | Pro | Asn | Arg | Ile | Val | Met | Ser | Gly | Gly | Ala | Thr |
| | | | 120 | | | | 125 | | | | | 130 |

```
AAG TTC GAT CCC AAC CGC ATT GTG ATG AGT GGT GGG GCA ACC    576
Lys Phe Asp Pro Asn Arg Ile Val Met Ser Gly Gly Ala Thr
            120             125                     130

GGA GCT CAT GAA ACT CTG GCC TTC TGT TTA GCT GAC CCT GAA    618
Gly Ala His Glu Thr Leu Ala Phe Cys Leu Ala Asp Pro Glu
            135                 140

GAT GCG TTT TTG GTA CCC ACA CCA TAT TAT CCA GGA TTT GAT    660
Asp Ala Phe Leu Val Pro Thr Pro Tyr Tyr Pro Gly Phe Asp
145             150                 155

CGG GAT TTG AGG TGG CGA ACA GGG ATG CAA CTT CTT CCA ATT    702
Arg Asp Leu Arg Trp Arg Thr Gly Met Gln Leu Leu Pro Ile
            160             165             170

GTT TGT CGC AGC TCC AAT GAT TTT AAG GTC ACT AAA GAA TCC    744
Val Cys Arg Ser Ser Asn Asp Phe Lys Val Thr Lys Glu Ser
            175                 180             185

ATG GAA GCT GCT TAT CAG AAA GCT CAA GAA GCC AAC ATC AGA    786
Met Glu Ala Ala Tyr Gln Lys Ala Gln Glu Ala Asn Ile Arg
                190             195                 200

GTA AAG GGG TTC CTC TTA AAT AAT CCA TCA AAT CCA TTG GGA    828
Val Lys Gly Phe Leu Leu Asn Asn Pro Ser Asn Pro Leu Gly
            205                 210

ACT GTT CTT GAC AGG GAA ACT TTG ATT GAT ATA GTC ACA TTC    870
Thr Val Leu Asp Arg Glu Thr Leu Ile Asp Ile Val Thr Phe
215             220                 225

ATC AAT GAC AAA AAT ATC CAC TTG ATT TGT GAT GAG ATA TAT    912
Ile Asn Asp Lys Asn Ile His Leu Ile Cys Asp Glu Ile Tyr
        230             235                 240

TCT GCC ACC GTC TTC AGC CAG CCC GAA TTC ATC AGC ATC TCT    954
Ser Ala Thr Val Phe Ser Gln Pro Glu Phe Ile Ser Ile Ser
            245                 250             255

GAA ATA ATT GAG CAT GAT GTT CAA TGC AAC CGT GAT CTC ATA    996
Glu Ile Ile Glu His Asp Val Gln Cys Asn Arg Asp Leu Ile
                260             265             270
```

FIGURE 2 (continued)

| | | | | | | | | | | | | |
|---|---|---|---|---|---|---|---|---|---|---|---|---|
| CAT | CTT | GTG | TAT | AGC | CTG | TCC | AAG | GAC | TTG | GGC | TTC | CCT | GGA | 1038 |
| His | Leu | Val | Tyr | Ser | Leu | Ser | Lys | Asp | Leu | Gly | Phe | Pro | Gly |
| | | | | 275 | | | | 280 | | | | |

```
CAT CTT GTG TAT AGC CTG TCC AAG GAC TTG GGC TTC CCT GGA    1038
His Leu Val Tyr Ser Leu Ser Lys Asp Leu Gly Phe Pro Gly
                275                 280

TTC AGA GTT GGC ATT TTG TAT TCA TAT AAT GAC GCT GTT GTC    1080
Phe Arg Val Gly Ile Leu Tyr Ser Tyr Asn Asp Ala Val Val
285                 290                 295

AGC TGT GCT AGA AAA ATG TCG AGT TTC GGC CTT GTT TCA ACA    1122
Ser Cys Ala Arg Lys Met Ser Ser Phe Gly Leu Val Ser Thr
        300                 305                 310

CAA ACT CAG CAT CTG ATT GCA TCA ATG TTA TCG GAC GAA GCA    1164
Gln Thr Gln His Leu Ile Ala Ser Met Leu Ser Asp Glu Ala
            315                 320                 325

TTT ATG GAC AAA ATC ATT TCC ACG AGC TCA GAG AGA TTA GCT    1206
Phe Met Asp Lys Ile Ile Ser Thr Ser Ser Glu Arg Leu Ala
                330                 335                 340

GCA AGG CAT GGT CTT TTC ACA AGA GGA CTT GCT CAA GTA GGC    1248
Ala Arg His Gly Leu Phe Thr Arg Gly Leu Ala Gln Val Gly
                    345                 350

ATT GGC ACC TTA AAA AGC AGT GCG GGC CTT TAT TTC TGG ATG    1290
Ile Gly Thr Leu Lys Ser Ser Ala Gly Leu Tyr Phe Trp Met
355                 360                 365

GAC TTA AGG AGA CTC CTC AGG GAG TCC ACA TTT GAG GCA GAA    1332
Asp Leu Arg Arg Leu Leu Arg Glu Ser Thr Phe Glu Ala Glu
        370                 375                 380

ATG GAA CTT TGG AGG ATC ATA ATA CAT GAA GTC AAG CTC AAT    1374
Met Glu Leu Trp Arg Ile Ile Ile His Glu Val Lys Leu Asn
                385                 390                 395

GTT TCA CCA GGC TTA TCT TTC CAT TGC TCA GAA CCA GGA TGG    1416
Val Ser Pro Gly Leu Ser Phe His Cys Ser Glu Pro Gly Trp
                400                 405                 410

TTC AGA GTT TGC TTT GCC AAC ATG GAC GAC GAA AGT GTG AGA    1458
Phe Arg Val Cys Phe Ala Asn Met Asp Asp Glu Ser Val Arg
                415                 420
```

FIGURE 2 (continued)

```
GTT GCT CTC AGA AGA ATC CAC AAA TTT GTG CTT GTT CAG GGC              1500
Val Ala Leu Arg Arg Ile His Lys Phe Val Leu Val Gln Gly
425             430                 435

AAG GCA ACA GAG CCA ACA ACT CCA AAG AGT CGC TGC GGA AGC              1542
Lys Ala Thr Glu Pro Thr Thr Pro Lys Ser Arg Cys Gly Ser
    440             445                 450

AGC AAA CTT CAA CTC AGC TTA TCT TTC CGC AGA TTG GAC GAA              1584
Ser Lys Leu Gln Leu Ser Leu Ser Phe Arg Arg Leu Asp Glu
        455             460                 465

AGG GTG ATG GGA TCG CAT ATG ATG TCC CCT CAC TCC CCG ATG              1626
Arg Val Met Gly Ser His Met Met Ser Pro His Ser Pro Met
            470             475                 480

GCT TCA CCT TTG GTT CGG GCT ACA TAAATCATTT CTTGATCAGA                1670
Ala Ser Pro Leu Val Arg Ala Thr
                485

TCATATAGCA AAGATTCCTG AGTAAATACT CGAAACCCTT TCTGGATAAC               1720

TGAAAAGAGA GTTGTTGATT CTTTGCTGTA TCATACAAAC ACGTTACAGG               1770

CATTTTTTGG CCATCTGATG CGTGCAAATT GCATCAAATG CTTTTATTAT               1820

TGTCATATTC ATTTGTGTAC CTTGGTTTTC CTTGCCCTTC AGTCCTCCTT               1870

GTTTTTTGTT TCTTTGTTAT TATTTCTTC CAGTTGATCA GTTAAACGAA                1920

GGAAGCTCAA TTGTTTCAAG CTATTAGTAA CAGATCATTT TGTAATAGCA               1970

ATAGTTTCAG GATTCTGAAA TGAAAGTTTA TCATTTTTCC ATCATTTTAA               2020

AAAAAAAAAA AAAAAAAAA                                                 2040
```

FIGURE 3: DEDUCED PROTEIN SEQUENCE OF THE COFFEE FRUIT-EXPRESSED ACC OXIDASE cDNA (SEQ ID NO:12)

```
Met Ala Thr Phe Pro Leu Ile Asp Met Glu Lys Leu Asp Gly Glu
 1           5                  10                  15

Glu Arg Ala Ala Thr Met Gly Val Ile Lys Asp Ala Cys Glu Ser
            20                  25                  30

Trp Gly Phe Phe Glu Val Leu Asn His Gly Ile Ser Asn Glu Leu
            35                  40                  45

Met Asp Thr Val Glu Arg Leu Thr Lys Glu His Tyr Lys Lys Cys
            50                  55                  60

Met Glu Leu Lys Phe Lys Glu Met Val Glu Ser Lys Glu Leu Glu
            65                  70                  75

Ala Val Gln Thr Glu Ile Asn Asp Leu Asp Trp Glu Ser Thr Phe
            80                  85                  90

Phe Leu Arg His Leu Pro Val Ser Asn Ile Ser Glu Val Pro Asp
            95                 100                 105

Leu Asp Asp Glu Tyr Arg Lys Val Met Lys Glu Phe Ala Leu Gln
           110                 115                 120

Leu Glu Lys Leu Ala Glu Leu Leu Leu Asp Leu Leu Cys Glu Asn
           125                 130                 135

Leu Gly Leu Glu Lys Gly Tyr Leu Lys Lys Ala Phe Tyr Gly Thr
           140                 145                 150

Lys Gly Pro Thr Phe Gly Thr Lys Val Ser Asn Tyr Pro Pro Cys
           155                 160                 165

Pro Arg Pro Glu Leu Ile Lys Gly Leu Arg Ala His Thr Asp Ala
           170                 175                 180

Gly Gly Ile Ile Leu Leu Phe Gln Asp Asp Lys Val Ser Gly Leu
           185                 190                 195

Gln Leu Leu Lys Asp Gly Glu Trp Val Asp Val Pro Pro Met Arg
           200                 205                 210

His Ser Ile Val Ile Asn Ile Gly Asp Gln Leu Glu Val Ile Thr
           215                 220                 225
```

FIGURE 3 (continued)

```
Asn Gly Lys Tyr Lys Ser Val Met His Arg Val Ile Ala Gln Pro
            230             235             240

Asp Gly Asn Arg Met Ser Leu Ala Ser Phe Tyr Asn Pro Gly Ser
            245             250             255

Asp Ala Val Ile Tyr Pro Ala Pro Ala Leu Val Glu Lys Glu Ala
            260             265             270

Glu Asp Lys Gln Ile Tyr Pro Lys Phe Val Phe Glu Asp Tyr Met
            275             280             285

Lys Leu Tyr Ala Gly Leu Lys Phe Gln Ala Lys Glu Pro Arg Phe
            290             295             300

Glu Ala Met Lys Ala Val Glu Ser Thr Val Asn Leu Gly Pro Ile
            305             310             315

Ala Thr Val
        318
```

FIGURE 4: DNA SEQUENCE OF THE COFFEE FRUIT-EXPRESSED ACC OXIDASE cDNA (SEQ ID NO:13)

```
TGTAAACGAA GCATAAGCAC AAGCAAACAC AAACTAGAAA GAGAG ATG               48
                                                   Met
                                                     1

GCT ACA TTC CCC CTA ATC GAC ATG GAG AAG CTT GAC GGT GAA             90
Ala Thr Phe Pro Leu Ile Asp Met Glu Lys Leu Asp Gly Glu
              5                  10                  15

GAG AGG GCT GCC ACT ATG GGA GTC ATA AAA GAT GCT TGT GAA            132
Glu Arg Ala Ala Thr Met Gly Val Ile Lys Asp Ala Cys Glu
                     20                  25

AGC TGG GGC TTC TTT GAG GTG TTG AAT CAT GGG ATA TCT AAT            174
Ser Trp Gly Phe Phe Glu Val Leu Asn His Gly Ile Ser Asn
30                       35                  40

GAG CTC ATG GAC ACA GTG GAG AGG CTA ACA AAG GAG CAT TAC            216
Glu Leu Met Asp Thr Val Glu Arg Leu Thr Lys Glu His Tyr
         45                  50                  55

AAG AAA TGT ATG GAA CTA AAG TTC AAG GAA ATG GTG GAG AGC            258
Lys Lys Cys Met Glu Leu Lys Phe Lys Glu Met Val Glu Ser
             60                  65                  70

AAG GAA TTG GAA GCT GTT CAG ACT GAG ATC AAT GAT TTG GAC            300
Lys Glu Leu Glu Ala Val Gln Thr Glu Ile Asn Asp Leu Asp
                 75                  80                  85

TGG GAA AGT ACC TTC TTC TTG CGC CAT CTT CCT GTT TCC AAC            342
Trp Glu Ser Thr Phe Phe Leu Arg His Leu Pro Val Ser Asn
                     90                  95

ATC TCA GAA GTC CCT GAT CTT GAT GAT GAA TAC AGA AAG GTT            384
Ile Ser Glu Val Pro Asp Leu Asp Asp Glu Tyr Arg Lys Val
100                     105                 110

ATG AAG GAA TTT GCG TTG CAA CTT GAG AAA CTA GCA GAG CTC            426
Met Lys Glu Phe Ala Leu Gln Leu Glu Lys Leu Ala Glu Leu
        115                 120                 125

CTG TTG GAC TTG CTA TGC GAG AAC CTT GGC CTA GAG AAA GGC            468
Leu Leu Asp Leu Leu Cys Glu Asn Leu Gly Leu Glu Lys Gly
            130                 135                 140
```

FIGURE 4 (continued)

| | | | | | | | | | | | | |
|---|---|---|---|---|---|---|---|---|---|---|---|---|
| TAT | CTG | AAG | AAA | GCC | TTC | TAT | GGC | ACC | AAA | GGA | CCA | ACC | TTT | 510 |
| Tyr | Leu | Lys | Lys | Ala | Phe | Tyr | Gly | Thr | Lys | Gly | Pro | Thr | Phe |
| | | | 145 | | | | 150 | | | | | 155 |

```
TAT CTG AAG AAA GCC TTC TAT GGC ACC AAA GGA CCA ACC TTT        510
Tyr Leu Lys Lys Ala Phe Tyr Gly Thr Lys Gly Pro Thr Phe
            145                 150                 155

GGC ACC AAA GTC AGC AAT TAC CCT CCA TGC CCT CGT CCA GAA        552
Gly Thr Lys Val Ser Asn Tyr Pro Pro Cys Pro Arg Pro Glu
            160                 165

CTG ATC AAG GGC CTC CGG GCA CAC ACC GAT GCC GGC GGC ATC        594
Leu Ile Lys Gly Leu Arg Ala His Thr Asp Ala Gly Gly Ile
170             175                 180

ATC CTG CTG TTC CAG GAT GAC AAG GTC AGC GGT CTC CAG CTC        636
Ile Leu Leu Phe Gln Asp Asp Lys Val Ser Gly Leu Gln Leu
        185                 190                 195

CTC AAG GAT GGT GAA TGG GTG GAT GTT CCG CCT ATG CGC CAC        678
Leu Lys Asp Gly Glu Trp Val Asp Val Pro Pro Met Arg His
            200                 205                 210

TCC ATT GTA ATC AAC ATC GGC GAC CAA CTT GAG GTA ATC ACA        720
Ser Ile Val Ile Asn Ile Gly Asp Gln Leu Glu Val Ile Thr
                215                 220                 225

AAT GGA AAA TAC AAG AGT GTG ATG CAC CGG GTG ATA GCT CAA        762
Asn Gly Lys Tyr Lys Ser Val Met His Arg Val Ile Ala Gln
            230                 235

CCA GAT GGG AAC AGA ATG TCA CTA GCA TCA TTC TAC AAT CCA        804
Pro Asp Gly Asn Arg Met Ser Leu Ala Ser Phe Tyr Asn Pro
240                 245                 250

GGA AGT GAT GCA GTG ATC TAT CCA GCA CCG GCA TTG GTT GAG        846
Gly Ser Asp Ala Val Ile Tyr Pro Ala Pro Ala Leu Val Glu
        255                 260                 265

AAA GAG GCA GAG GAC AAG CAG ATA TAT CCC AAG TTT GTG TTC        888
Lys Glu Ala Glu Asp Lys Gln Ile Tyr Pro Lys Phe Val Phe
            270                 275                 280

GAG GAC TAC ATG AAG CTC TAT GCT GGC CTT AAG TTC CAA GCT        930
Glu Asp Tyr Met Lys Leu Tyr Ala Gly Leu Lys Phe Gln Ala
                285                 290                 295
```

FIGURE 4 (continued)

```
AAA GAG CCC AGG TTT GAA GCC ATG AAG GCC GTG GAA AGC ACC         972
Lys Glu Pro Arg Phe Glu Ala Met Lys Ala Val Glu Ser Thr
                300                 305

GTA AAC TTG GGT CCA ATC GCA ACT GTT TGAGATAATA CACGCTTTGA      1019
Val Asn Leu Gly Pro Ile Ala Thr Val
310                 315

TCTGCTGCTG TCTTATAATG CGCGTTTGCG TAATCATATC CTAGCATAGT         1069

ATATCTGAGA TCTGAGTCTG TATTGTGGTG TGAGTTTGGT TTAGCCCCTT         1119

GTTAATGCTT GGATTGGACT AGTTAAATGT GGAGCTGGTT TGTTAGATAA         1169

GATAGTCTTG CCAGGATCTT TGAGTAAATA TGATTCTGCG GAAGTCTGCG         1219

GTGAATGATA ACGTGTAAAG CAATCCGAAA GTTACCTTTC TGGGGCTTTG         1269

TCATATGCAA TGGAGAAGGA ATCTTCCAAA AAAAAAAAAA AAAAAAAAA          1319

A                                                              1320
```

Coffee ACC synthase antisense cDNA in pKR1

Coffee ACC synthase sense cDNA in pKR1

Coffee ACC oxidase antisense cDNA in pKR1

Coffee ACC oxidase sense cDNA in pKR1

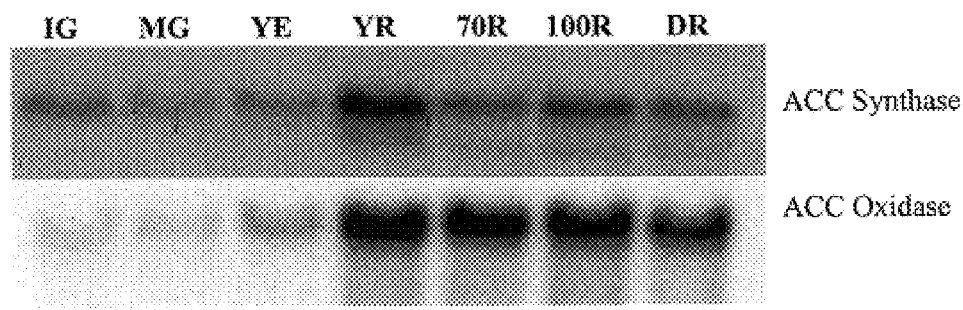
FIG. 9  Expression of ACC synthase and ACC oxidase message in ripening coffee cherries. Twenty μg total RNA from cherries, representing seven stages of maturity were loaded per lane in 1.5% denaturing formaldehyde agarose gel (Fourney et al., 1988). The lanes are (1) immature green (IG); (2) mature green (MG); (3) yellow (YE); (4) yellow-red (YR); (5) 70% red (70R); (6) 100% red (100R); and (7) dark red (DR).

PURIFIED PROTEINS, RECOMBINANT DNA SEQUENCES AND PROCESSES FOR CONTROLLING THE RIPENING OF COFFEE PLANTS

This application is a continuation-in-part of Ser. No. 08/695,412 filed Aug. 12, 1996 now U.S. Pat. No. 5,874, 269, which is a continuation-in-part of Ser. No. 08/485,107 filed Jun. 7, 1995 now U.S. Pat. No. 5,767,376.

BACKGROUND OF THE INVENTION

Coffee is prepared from the roasted beans of the plants of the genus Coffea, generally from the species *C. arabica* (Caturra coffee) and *C. canephora* (Robusta coffee), and hybrids of these. Beans are the seeds of the coffee plant and are obtained by processing the coffee fruit, ideally the mature coffee fruit which commands the best price due to its superior quality. In order to obtain high quality "gourmet" coffee, it was considered necessary in the past to pick the coffee tree fruit by hand because the fruits of a coffee tree do not ripen uniformly and, thus, there are both mature and immature fruit on the same tree. This did not previously present a serious problem, as most coffee is grown in areas of the world where labor is plentiful and not expensive. However, recently, a lack of abundant and inexpensive labor has become a major contributor to decreased coffee production. In order to increase productivity, countries in some regions of the world, such as the largest coffee producing country, Brazil, have resorted to strip harvesting where workers rapidly remove all fruit from a branch whether ripe or unripe. The speed of harvesting is thus increased, but the yield of the highest quality beans is decreased because much of the harvested fruit is immature (green).

The lack of uniform ripening of coffee fruit on the tree has also seriously limited the effectiveness of mechanical harvesting. The force required to remove mature fruit (cherry) from the tree is similar to the force required to remove green fruit. Thus, mechanical harvesters do not distinguish well between green fruit and cherry and a large amount of immature fruit is harvested along with mature fruit. If coffee fruit ripening could be controlled so that all fruit ripened at one time, both the strip method of hand harvesting and mechanical harvesting would be much more efficient and a higher percentage of the harvested fruit would be in the higher quality grades, resulting in increased profitability of coffee production.

Ripening of fruit involves a number of changes in the fruit. In fleshy fruits, chlorophyll is degraded and other pigments often form, changing the color of the fruit. Simultaneously, the fleshy part softens as a result of the enzymatic digestion of pectin, the principal component of the middle lamella of the cell wall, and starches and organic acids are metabolized into sugars. Fruits are divided into two major groups, based on the respiratory behavior observed during the ripening process. In the climacteric fruits, such as tomatoes, avocados, bananas, apples and pears (i.e., pome fruits), and papaya, there is a large increase in respiration (i.e., a large increase in oxygen uptake termed the "climacteric rise") concomitant with a burst of ethylene synthesis, producing marked changes in fruit composition and texture. In these fruits, the "climacteric" is required for the final stages of ripening when softening and development of color and flavor occurs. Other plants do not have a climacteric and ethylene does not seem to be important in their fruit ripening. Such fruits that show a steady decline or gradual ripening are called "non-climacteric fruits" (e.g., citrus, grapes, watermelon, cherries, pineapples, strawberries, and most vegetable crops such as carrots, onions, celery, spinach, crucifers, peas and beans).

Once climacteric fruit reach a certain stage of maturity, it is known that they can be induced to ripen by the exogenous application of ethylene, such as during storage and/or transport. Techniques to avoid exposure of climacteric fruits to ethylene until just before marketing have been used to control and regulate the timing of the ripening process, and have had a major impact on the quality of fruit sold. For example, tomatoes are often picked when they are green, and then stored in the absence of ethylene until just before marketing, at which time they are exposed to exogenous ethylene to induce simultaneous ripening. Exogenous ethylene has also been used commercially to promote loosening of fruit such as cherries, blackberries, grapes, and blueberries, thereby facilitating mechanical harvesting of these fruit crops.

In view of the foregoing, it would be very advantageous to be able to characterize coffee plants as to whether or not they are climacteric and, if shown to be climacteric, to control the ripening of coffee fruit by exogenously applied ethylene. Until the investigations described herein and in our co-owned U.S. Pat. No. 5,874,269, the disclosure of which is hereby incorporated by reference in its entirety, it was not known whether coffee fruit is climacteric or non-climacteric. Although it was observed that coffee fruit ripened in response to ethylene after reaching a certain stage of development [Crisosto, C. H., et al., *J. Haw. Pac. Agri.* 3:13–17 (1991)], it was not possible to measure ethylene evolution or a respiration increase in ripening fruit. This may be because of the small size of the fruit and the lack of uniformity of ripening.

The biosynthesis of ethylene begins with the reaction of methionine and ATP to form S-adenosylmethionine (SAM). The enzyme ACC synthase catalyzes the conversion of SAM to 1-aminocyclopropane-1-carboxylic acid (ACC). In most plants this is the rate limiting step. The ACC is then converted to ethylene, in a reaction that is catalyzed by ACC oxidase [Yang and Hoffman, *Ann. Rev. Physiol.* 35, 155 (1984)].

It is well known that ethylene is related to various events in plant growth and development, including fruit ripening, seed germination, leaf and flower senescence and abscission, and root and leaf growth. Ethylene production is strictly regulated by the plant and can be induced by a variety of external stress factors, including the application of auxins, wounding, anaerobic conditions, viral infection, chilling, drought, ions such as cadmium and lithium ions, and the like.

Recombinant DNA technology has been used to isolate a number of ACC synthase genes from, for example, rice, petunia, winter squash, zucchini, tomato, tobacco, mung bean, soybean, and apple. Examples of these ACC synthase genes are described in our co-owned U.S. Pat. No. 5,767, 376, the disclosure of which related to these examples is hereby incorporated by reference. However, with the exception of the apple and a subset of the tomato ACC synthase gene sequences, none of the described ACC synthase genes are involved with the ripening of fruit. Therefore, ethylene production in plants is apparently governed by a family of ACC synthase genes, at least in the above examples, not all of which are expressed during fruit ripening, e.g., some would be active in wound response, and the like. Similarly, it is considered likely that there is a family of ACC oxidase genes in plants that are variously active at different stages of plant growth and fruit ripening. The DNA sequences of the members of the ACC synthase gene family or the members of the ACC oxidase gene family in a plant such as coffee are therefore thought to be different from each other, although they would be related. For example, ACC synthase is encoded by at least six divergent genes in tomato. J. E. Lincoln et al. [*J. Biol. Chem.* 268 (no. 26), pp. 19422+, September 1993] compared the gene sequences of two ACC synthases thought to be involved in fruit ripening in tomatoes and found a sequence homology of only 71%. Two other ACC synthase genes from tomato had a sequence homology of 96% with each other. However, the sequence homology between the two sets of ACC synthase genes was only 68% and they had only a 51% sequence homology with an ACC synthase gene from rice. It is similarly expected that the genes coding for ACC synthases involved in fruit ripening from different varieties of coffee, such as *C. arabica, C. canephora,* and blends of these, such as the Timor hybrid and the like, would show a high sequence homology, but would not be identical. Moreover, the findings in the tomato demonstrate the importance of using ripening coffee fruit tissue in order to be able to isolate genes coding for any ACC synthase(s) that are expressed during fruit ripening, because these genes are likely to be different than ACC synthase genes expressed during other phases of the growth of the coffee tree.

A strategy for determining whether coffee trees are climacteric would be to measure the level of expression of the "fruit ripening" ACC synthase gene and/or the "fruit ripening" ACC oxidase gene, i.e., by measuring the levels of messenger RNA (mRNA) coding for each of these enzymes, during fruit ripening. Once it has been established that coffee plants are climacteric, a further strategy to control the ripening of coffee fruit would be to prevent synthesis of the specific ACC synthase enzyme and/or the ACC oxidase enzyme in the pathway for ethylene biosynthesis during fruit ripening and to apply exogenous ethylene to synchronize and control fruit ripening in coffee plants.

Thus, in one embodiment of the invention, coffee plants are genetically altered to eliminate synthesis of ACC synthase; in another embodiment, ACC oxidase synthesis is eliminated; and in another embodiment, synthesis of both enzymes is eliminated. In the presently preferred embodiments, synthesis of one or both of these enzymes is eliminated by transforming coffee plants with a nucleic acid sequence that codes on transcription for an RNA that is antisense to the mRNA that codes on expression for the enzyme whose synthesis is to be eliminated. See Oeller et al., *Science* 254:437 (1991), who reported controlling ripening of tomatoes using a similar strategy. In another embodiment of the invention, synthesis of one or both of ACC synthase and ACC oxidase is eliminated by transforming coffee plants with a nucleic acid sequence that codes on transcription for an RNA that is sense to the mRNA that codes on expression for the enzyme whose synthesis is to be eliminated. Such a strategy is well known and is termed co-suppression or sense-suppression.

Although recombinant DNA technology has been used to isolate a number of ACC synthase and ACC oxidase genes from other plants, it was not until the present invention that genes for ACC synthase and ACC oxidase enzymes that are active in coffee fruit ripening have been identified, isolated and sequenced. An important reason why these genes have not been previously identified, isolated and sequenced is that coffee fruit contains high levels of phenolic compounds such as chlorogenic acid (5-O-caffeoylquinic acid), and high levels of carbohydrates. For example, depending on the coffee variety, ripe seeds of *Coffea arabica* L. contain between 4% and 8% dry weight of chlorogenic acid. [Aerts, R. J. and T. W. Baumann. *J. Exp. Botany* 45, 497–503 (1994)]. In another study of 12 different cultivars of *Coffea arabica* L, the average content of phenolic compounds tentatively identified by HPLC in fresh coffee pulp was 42.2% chlorogenic acid, 21.6% epicatechin, 5.7% isochlorogenic acid I, 19.3% isochlorogenic acid II, 4.4% isochlorogenic acid III, 2.2% catechin, 2.1% rutin, 1.6% protocatechuic acid, and 1.0% ferulic acid. When the percentages of chlorogenic and isochlorogenic acids were added to the corresponding one of epicatechin for each cultivar, it was found that these acids made up between 92.0% and 98.4% of the total of identified phenolic compounds. [Ramirez-Martinez, J. R., *J. Sci. Food and Agriculture* 43, 135–144 (1988)]. In another study reported at the 13th International scientific colloquium on coffee in 1989, Ramirez-Martinez reported the nature and content of phenolic acids extracted with hot 70% methanol from sun-dried pulp of Robusta coffee (*Coffea canephora*), Red Bourbon, Caturra (*Coffea arabica*), Timor hybrid (*C. canephora×C. arabica*) and Catimor (Timor hybrid×Red Caturra) berries (ripe coffee seeds), the total chlorogenic acid content was 4 times higher in Robusta (1.6%) than in Timor hybrid and Catimor, whereas the *C. arabica* cultivars had intermediate values. Therefore, it appears that the coffee fruit from most, if not all, commercially important species of coffee contain high levels of phenolic compounds.

The combination in the coffee fruit of high levels of phenolics and high levels of carbohydrates makes it very difficult to obtain clean preparations of RNA from this tissue. For example, homogenization of tissue in homogenization buffers typically used to obtain RNA from non-coffee fruit tissues cannot be used for obtaining RNA from coffee fruit because the darkly colored polyphenols in the coffee fruit adhere to the nucleic acids in the tissue during grinding, with the result that the tissue turns dark brown to black. The adhered polyphenol compounds prevent, for example, cutting of the nucleic acids with restriction enzymes, copying of the mRNA with reverse transcriptase to produce a cDNA library, and the like. Moreover, the high levels of carbohydrates prevent the use of a typical chloroform/alcohol-precipitation of RNA from the tissue homogenate because the carbohydrates are co-precipitated with the RNA to produce a carbohydrate-RNA "glob".

Thus, in order to overcome the problems inherent in obtaining clean RNA preparations from coffee fruit, it is necessary to develop new methods for extraction of the RNA that address the high levels of phenolics and carbohydrates in coffee fruit tissue.

SUMMARY OF THE INVENTION

The present invention establishes that coffee fruits are climacteric and, therefore, like other climacteric fruits, it is possible to regulate coffee fruit ripening by the application of exogenous ethylene. By developing techniques to isolate substantially pure RNA from coffee fruit, it has been demonstrated herein that mRNA coding for coffee fruit-expressed ACC synthase is present in a small amount in young fruit, and that the level of this ACC synthase mRNA increases rapidly as coffee fruit matures. It has also been demonstrated that accumulation of coffee fruit-expressed ACC oxidase mRNA is similar to that of the ACC synthase mRNA, except that the levels of expression are much higher. The rapid rise in the amount of both ACC synthase and ACC oxidase mRNA during the final stages of fruit ripening in coffee is indicative of a climacteric fruit. It is believed that this invention provides the first convincing evidence that coffee is a climacteric fruit.

Because of the improved methodology described herein for isolating substantially pure mRNA from coffee fruit, cDNA libraries have been constructed from which substantially pure nucleic acid sequences that code on expression for coffee fruit-expressed ACC synthase and ACC oxidase are isolated and sequenced. The invention further provides substantially pure coffee fruit-expressed ACC synthase and ACC oxidase. The invention further provides recombinant nucleic acid sequences, including hosts transformed with such sequences, for transforming coffee plants to suppress the expression of enzymes necessary for ethylene synthesis during coffee fruit ripening. The nucleic acid sequences and recombinant DNA molecules are characterized in that they code on expression for the enzymes ACC synthase or ACC oxidase that are elements of the pathway for ethylene biosynthesis in coffee fruit ripening.

In one embodiment of the invention, coffee plants are transformed with DNA constructs that comprise a transcriptional initiation (promoter) region operably linked to a nucleic acid sequence that codes on a transcription for an RNA that is complementary (antisense) to a substantial run of bases of a mRNA that codes for a coffee fruit-expressed ACC synthase and/or ACC oxidase. In another embodiment of the invention, coffee plants are transformed with DNA constructs that comprise a transcription promoter operably linked to a nucleic acid sequence that codes on transcription for an RNA that shows substantial homology (sense) to a substantial run of bases of the mRNA that codes for coffee fruit-expressed ACC synthase and/or ACC oxidase. Expression of sense or antisense nucleic acid sequences in the transformed plants eliminates the synthesis of ethylene during coffee fruit ripening, although other aspects of cellular metabolism are not affected.

Ripening of the fruit of the transformed plants can be regulated by exogenous ethylene. By application of ethylene to the entire plant, the entire plant will ripen at once, making manual and mechanical harvesting of coffee more productive.

BRIEF DESCRIPTION OF THE DRAWINGS

FIG. 1 represents the amino acid sequence of the coffee fruit-expressed ACC synthase deduced from the cDNA sequence shown in FIG. 2.

FIG. 2 represents the complete sequence of the cDNA encoding coffee fruit-expressed ACC synthase.

FIG. 3 represents the amino acid sequence of the coffee fruit-expressed ACC oxidase deduced from the cDNA sequence shown in FIG. 4.

FIG. 4 represents the sequence of the cDNA encoding coffee fruit-expressed ACC oxidase.

FIG. 9 illustrates the expression of ACC synthase and ACC oxidase mRNA in ripening coffee cherries. Twenty $\mu$g total RNA from cherries, representing seven stages of maturity were loaded per lane in 1.5% denaturing formaldehyde agarose gel [Fourney et al., Focus 10, 5–7 (1988)]. The lanes are (12) immature green (IG); (2) mature green (MG); (3) yellow (YE); (4) yellow-red (YR); (5) 70% red (70R); (6) 100% red (100R); and (7) dark red (DR).

DETAILED DESCRIPTION OF THE INVENTION

Definitions

Figure 5:
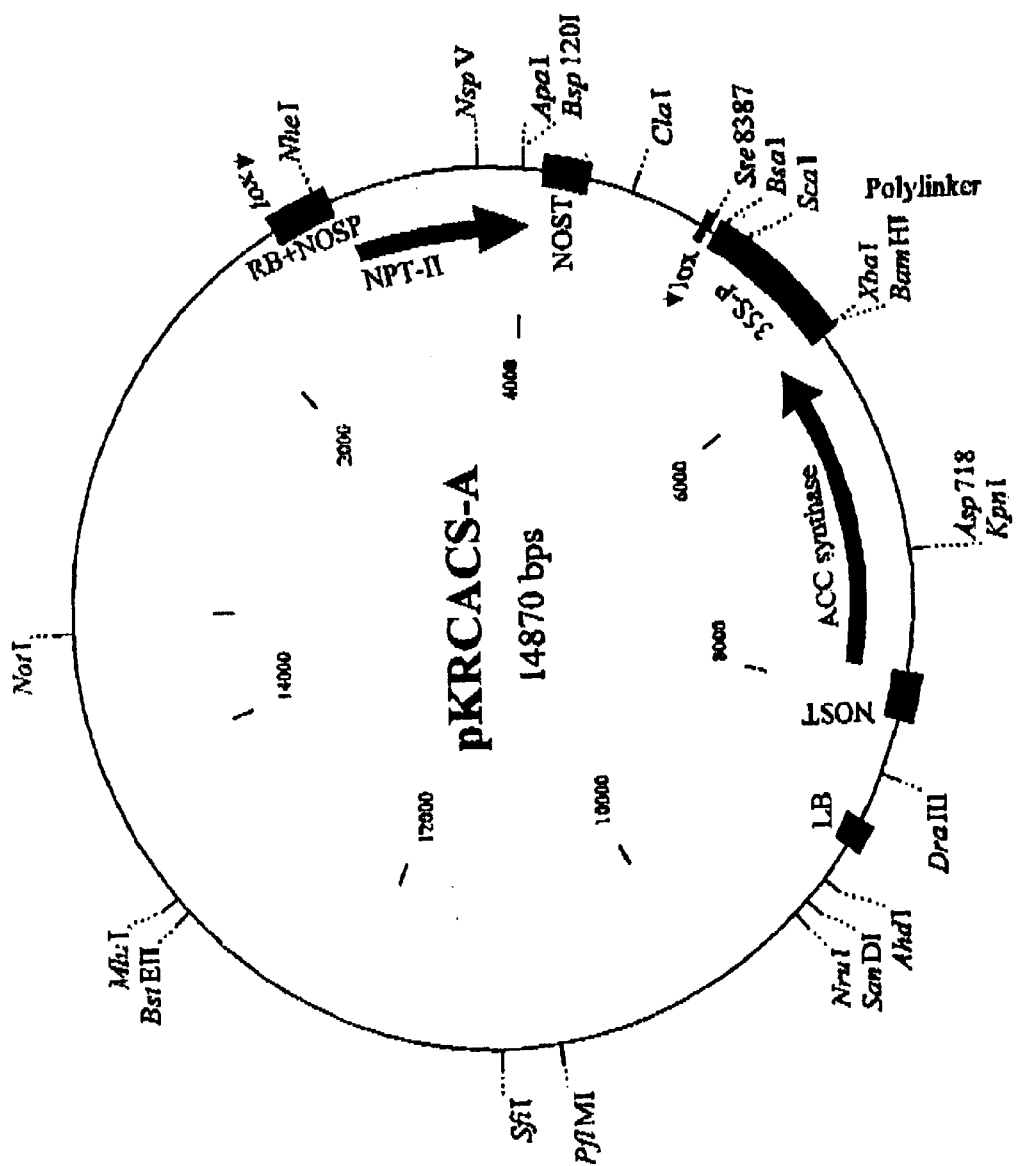
FIG. 5 is a schematic illustration showing the construction of the plasmid pKRCACS-A by the insertion of the coffee fruit-expressed ACC synthase cDNA in the inverted, antisense orientation into a pKR1 transformation vector. NOS= nopaline synthase; (35S-P)=cauliflower mosaic virus 35S promoter; and NPT II=neomycin phosphotransferase II.

To facilitate understanding of the invention, a number of terms are defined below.

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal, which also encodes the amino acid methionine ("MET").

Polypeptide—A linear array of amino acids connected one to the other by peptide bonds between the amino and carboxy groups of adjacent amino acids.

Genome—The entire DNA of a cell or a virus. It includes inter alia the structural gene coding for the polypeptides of the substance, as well as promoter, transcription and translation initiation and termination sites.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Antisense—The term "antisense", as used herein, is used in reference to RNA sequences which are complementary to a specific RNA sequence (e.g., mRNA). Antisense RNA may be produced by any method, including synthesis by splicing nucleic acid sequences that code for all or part of the specific RNA sequence in a reverse (inverted) orientation to a promoter which permits the synthesis of a coding sequence.

Sense—The term "sense", as used herein, is used in reference to a substantial run of RNA bases having essentially the same base sequence as a specific RNA sequence (e.g., mRNA). Sense RNA may be produced by any method, including synthesis by splicing nucleic acid sequences that code for all or part of the specific RNA sequence in a sense orientation to a promoter which permits the synthesis of a coding sequence.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TETR) transforms a cell previously sensitive to tetracycline into one which is resistant to it. A cell transformed by a plasmid is called a "transformant."

Vector—As used herein, the term "vector" is used in reference to nucleic acid molecules that transfer other nucleic acid segment(s) from one cell to another. The term "vehicle" is sometimes used interchangeably with "vector". A "transforming vector" is one which transforms a cell.

Operably linked—The linkage of nucleic acid sequences such that a nucleic acid molecule capable of directing the transcription of a given gene and/or the synthesis of a desired protein molecule.

Phage or Bacteriophage—Bacterial virus many of which consist of DNA sequences encapsidated in a protein envelope or coat ("capsid").

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

cDNA—A DNA strand complementary to an mRNA that codes for a particular polypeptide.

DETAILED DESCRIPTION OF THE INVENTION

A strategy for determining whether coffee trees are climacteric is to isolate and measure the levels of mRNA coding for coffee fruit-expressed ACC synthase and coffee fruit-expressed ACC oxidase. However, in order to isolate the mRNA from coffee fruit, it was necessary to develop improved techniques for obtaining highly purified mRNA from this tissue.

Isolation of Highly Purified mRNA from Coffee Fruit

In general, coffee fruit at various stages of development was harvested from coffee trees, based on their skin color and maturity. As the fruit ripens, the skin color of the coffee fruit is observed to change from "immature green", to "mature green", to yellow, to yellow-red, to red, to dark red. Seeds were removed from the coffee fruit at the various stages of development as judged by the skin color, and the fruit skin with remaining mesocarp tissue was frozen and ground into a fine powder which was then homogenized in a homogenization buffer.

As described above, coffee fruit tissue contains high levels of phenolics and carbohydrates that interfere with extraction of purified mRNA. For example, homogenization of tissue in homogenization buffers typically used to obtain RNA from non-coffee fruit tissues cannot be used for obtaining RNA from coffee fruit because the darkly colored polyphenols in the coffee fruit adhere to the nucleic acids in the tissue during grinding, with the result that the tissue turns dark brown to black. The adhered polyphenol compounds prevent, for example, cutting of the nucleic acids with restriction enzymes, copying of the mRNA with reverse transcriptase to produce a cDNA library, and the like. Therefore, the homogenization buffer had to be tailored to prevent the adherence of phenolics to the nucleic acids. It was discovered that adherence of the polyphenols could be prevented by the addition of a combination of antioxidants to an existing (known) RNA extraction buffer, in the concentrations described below in Example 1. In particular, it was discovered that the addition of a combination of thiorurea, β-mercaptoethanol and dithiothreitol (10 mM) to a standard RNA extraction buffer, in combination with a soluble form of polyvinylpyrrolidone (to trap phenolics), prevented the polyphenols present in the coffee fruit from adhering to the nucleic acid. It was further discovered that the problems of carbohydrate and phenolic compound contamination of the precipitated mRNA could be minimized by employing two precipitation steps, instead of one, i.e., a chloroform/ethanol precipitation of the specially-buffered homogenate selectively precipitated the phenolic compounds but not the RNA. The phenolic compounds were extracted into the organic phase and the RNA and carbohydrates remained in the aqueous phase. The aqueous phase was then subjected to an extraction with 3M sodium chloride and alcohol. This extraction precipitated the RNA exclusively.

Suppression of Synthesis of Coffee Fruit-expressed ACC Synthase and/or ACC Oxidase in Transformed Coffee Plants The strategy for controlling ethylene biosynthesis in coffee plants according to the present invention relates in the first instance to determination of the genes that code on expression for two enzymes in the ethylene pathway during coffee fruit ripening: ACC synthase and ACC oxidase. Transformation of wild type coffee plants with constructs containing either or both genes in an orientation that is antisense or sense to the normal genes is expected to block synthesis of the respective enzymes.

In general, to produce an antisense RNA transcript, nucleic acid sequences derived from the gene (or a naturally occurring allelic variant of the gene) whose expression is to be reduced (e.g., coffee fruit-expressed ACC synthase and/or ACC oxidase), are placed downstream of a transcription promoter in the opposite transcriptional orientation (relative to the direction of transcription of the endogenous gene present in the chromosome). The resulting antisense construct is introduced into the plant cell host where the antisense construct directs the transcription of antisense RNA transcripts. The antisense RNA transcript is complementary to the sense transcript produced by the endogenous gene in the plant. While not limiting the invention to any particular theory, it is believed that the antisense transcripts form a duplex with the sense transcripts, thereby preventing the splicing, transcription or translation of the sense (or endogenous RNA) transcript. In this manner a reduction in the function of the naturally existing RNA is achieved.

Inhibition or suppression of gene expression in plants can also be achieved by the introduction of nucleic acid sequences which direct the expression of "sense" transcripts which correspond to endogenously expressed RNA transcripts. This phenomenon, known as "co-suppression" is well known and co-suppression of a number of plant genes has been reported. Co-suppression or sense suppression may involve the coordinate repression (silencing) of a transgene and a homologous endogenous gene, or the repression of two homologous transgenes. While the invention is not limited to a particular theory, it is believed that co-suppression may involve post-transcriptional events, such as the induction of RNA degradation by the overexpression of a given transcript (due to expression of both the endogenous RNA and the transgene RNA transcripts). Additionally, the interaction of the transgene and the endogenous gene may occur on a DNA-DNA level which results in the methylation of the gene sequences; methylated gene sequences are often transcriptionally inactive in plants.

The choice of the transcription promoter in the nucleic acid construct depends on the type of host cell to be utilized. Promoters which are active in plant cells include the octopine synthase promoter, the nopaline synthase promoter and the mannopine synthase promoter from the Ti plasmid, ORF7, the 35S promoter from cauliflower mosaic virus (CaMV), the double 35S promoter (D35S), the ribulose-1, 3-biphosphate carboxylase small subunit promoter, and the phasolin promoter. Other promoters active in plant cells are known in the art. Preferably, the 35S promoter from cauliflower mosaic virus is used as a transcription promoter in the transformed coffee cells of the present invention.

Whether suppression of the expression of an endogenous gene is by antisense RNA or by co-suppression with sense RNA, it has been reported that it is not necessary to transform plant cells with a DNA construct that is as long as the relevant mRNA produced by the cell. (See, e.g., WO 91/01375, where DNA constructs containing a DNA sequence encoding RNA complementary to "a substantial run of bases" showing substantial homology to a mRNA encoding an enzyme involved in ethylene biosynthesis were produced and used to suppress ethylene biosynthesis in tomatoes). Preferably, the DNA constructs of the present invention comprise a base sequence at least 50 bases in length for transcription into antisense or sense RNA. For convenience, it is generally found to be suitable to use sequences between 100 to 1000 bp in length. There is no theoretical upper limit to the number of bases in the sequence; it may be as long as the relevant mRNA produced by the cell.

Transforming vectors containing the DNA constructs can be introduced into the coffee plant cells (e.g., embryonic cells, callus, protoplasts, and the like) by any of a variety of published techniques known to those skilled in the art. Exemplary techniques are microprojectile (biolistic) bombardment, co-cultivation with a plasmid-containing bacteria such as *Agrobacterium tumefaciens,* direct DNA uptake by protoplasts (often enhanced by the use of polyethylene glycol or electroporation), electrophoresis, microinjection, silicon carbide fibers, and the like.

A large number of vectors are available for replication in bacterial hosts. A number of these vectors are commercially available, such as λgt10 and 11, the pUC series, M13 series, pBR322, pBI-121, pKR1, pACYC184, or the like. The selection of the vector is dependent upon the convenience of preparation, availability, copy number, size, and the like. Preferred vectors for modification as transformation vectors for the coffee plant cells of the invention are pBI-121 and pKR1.

Elimination of the Activity of Coffee Fruit-expressed ACC Synthase and/or Coffee Fruit Expressed ACC Oxidase In order to isolate nucleic acid sequences coding on expression for an ACC synthase and an ACC oxidase necessary for production of ethylene involved in the fruit ripening stage of coffee plant development, a cDNA library was constructed from the total RNA isolated from coffee fruit tissue at various stages of ripeness. The cDNA library was then screened for cDNA specific to these enzymes with synthetic DNA probes containing nucleotide sequences expected to occur. These expected sequences were based on studies of nucleotide sequences that occur in genes that encode the respective enzymes in other climacteric plants and other plants. The cDNA corresponding to the gene encoding ACC synthase or ACC oxidase was identified and sequenced.

The cDNA encoding the mRNA for each enzyme was amplified using the polymerase chain reaction (PCR) and one or both cDNAs incorporated into a transformation vector which included an antibiotic resistance gene. Insertion of the cDNA sequence(s) into the vector was either in a sense direction or in an antisense direction (inverted orientation) relative to an adjacent cauliflower mosaic virus 35S promoter. The constructs were used to transform coffee plant leaf tissue which was then placed into tissue culture for development of callus. Presumptive successful incorporation of either vector or both vectors into the coffee plant cells was determined by growth of the cells in the presence of an antibiotic (e.g., kanamycin). Callus cells were then selected for further culture and induction of embryonic tissue. When sufficient tissue is obtained, the presence of the DNA construct(s) in the genome of the plant cells is confirmed by PCR and Southern blot analysis.

The transformed embryos are thereafter grown into novel coffee plants in which the expression of coffee fruit-expressed ACC synthase and/or ACC oxidase is eliminated, with the concomitant elimination of ethylene biosynthesis during coffee ripening. Ripening of the mature fruit of the transformed plants is initiated by the application of exogenous ethylene, such as exposure to ethylene gas.

Specific Embodiments of the Invention

In order to isolate ACC synthase and ACC oxidase gene sequences involved in the ripening of coffee, a cDNA library was prepared from a mixture of coffee fruit pericarp and mesocarp tissue at different stages of ripeness. Briefly, RNA was extracted from the tissue and mRNA containing poly $(A^+)$ tails was purified therefrom. A cDNA library was prepared from the poly $(A^+)$ mRNA using reverse transcriptase. Double stranded DNA was prepared using DNA polymerase I, and recovered by precipitation. The cDNA was fractionated and inserted into phage for amplification. The cDNA library was screened using a PCR product synthesized from first-strand cDNA made from the same mRNA used to construct the library, and degenerate oligonucleotide primers corresponding to consensus sequences derived from ACC synthase and ACC oxidase genes from other plants. Clones producing a cDNA containing either the sequences coding for ACC synthase or ACC oxidase were identified.

The cDNA corresponding to the gene encoding coffee fruit-expressed ACC synthase and/or ACC oxidase was used to transform coffee plant leaf tissue. A modified pBI-121 plasmid (pKR1) was used as a transforming vector. In one embodiment of the invention, the sequences corresponding to DNA that codes on expression for ACC synthase were inserted into the plasmid in an inverted orientation adjacent to a cauliflower mosaic virus 35S promoter to form the DNA construct "pKRCACS-A" illustrated in FIG. 5. RNA transcribed therefrom is complementary (antisense) to all or part of the mRNA that encodes the amino acid sequence of coffee fruit-expressed ACC synthase.

Figure 6:
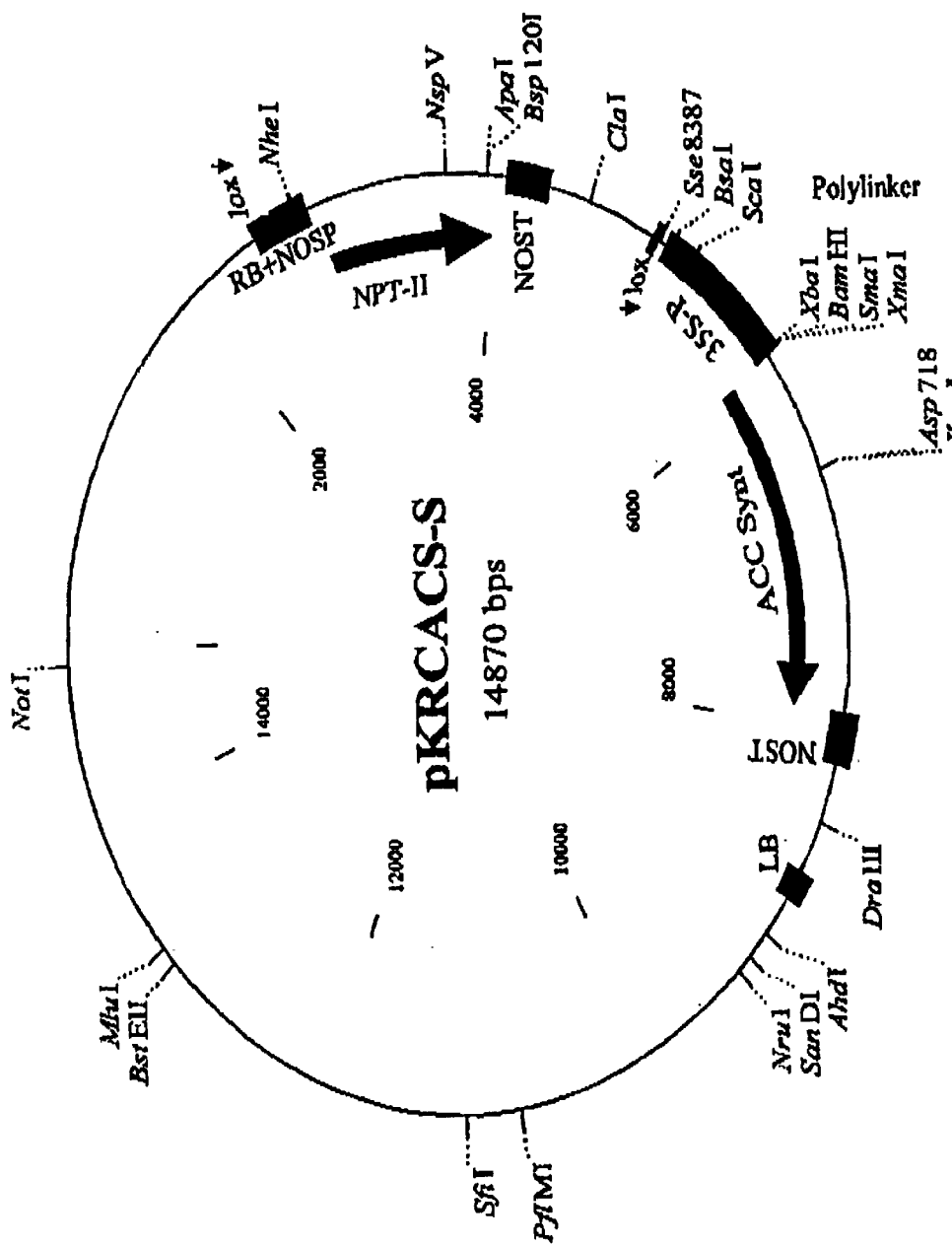
FIG. 6 is a schematic illustration showing the construction of the plasmid pKRCACS-S by the insertion of the coffee fruit-expressed ACC synthase cDNA in the sense orientation into a pKR1 transformation vector.

In another embodiment of the invention, the sequences corresponding to the DNA coding on expression for coffee fruit-expressed ACC synthase was inserted into the plasmid in a sense orientation adjacent to the cauliflower mosaic virus 35S promoter to form the DNA construct "pKRCAC-S", illustrated in FIG. 6. RNA transcribed therefrom has substantially the same base sequence as all or part of the mRNA that encodes the amino acid sequence of coffee fruit-expressed ACC synthase.

Figure 7:
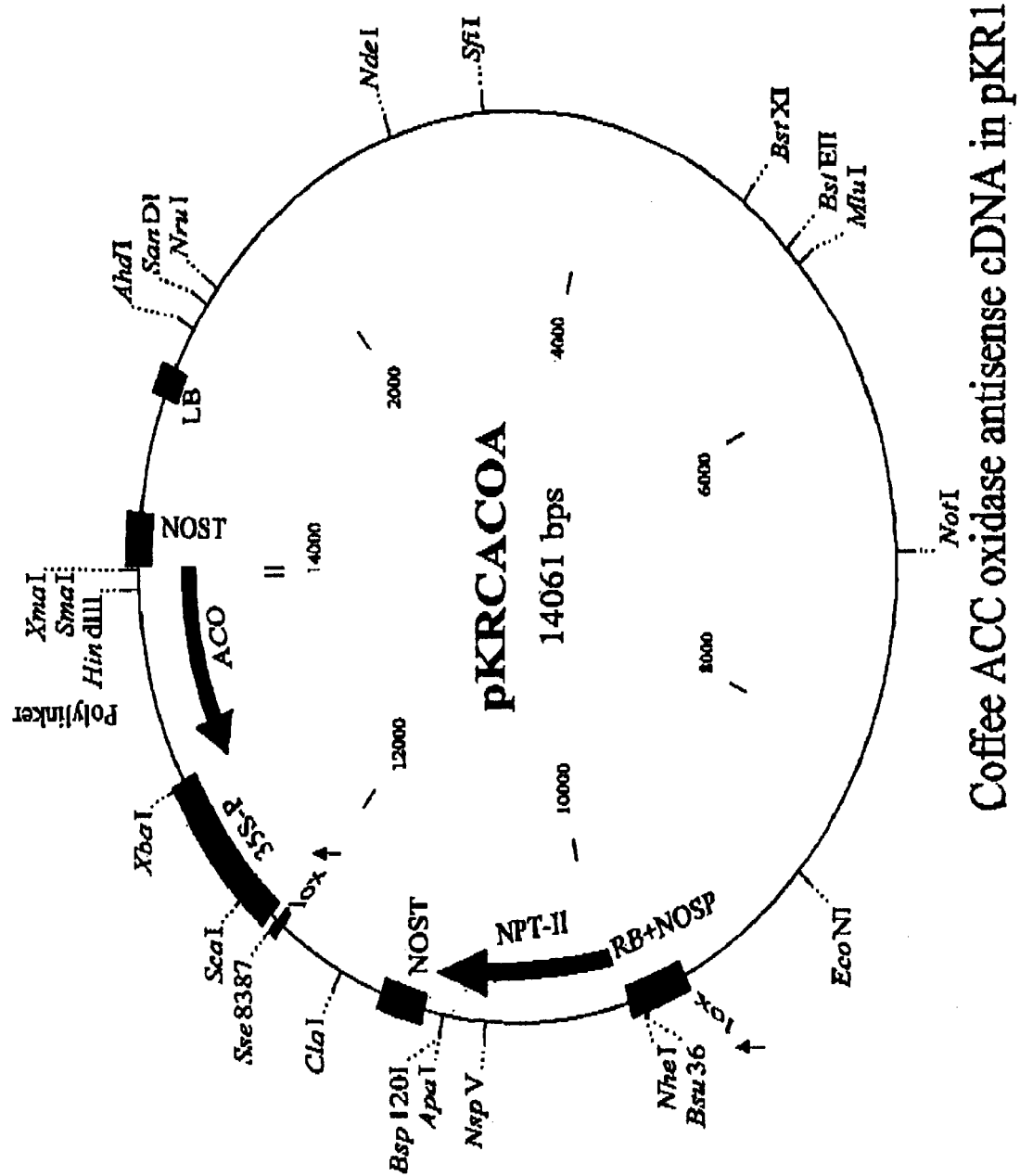
FIG. 7 is a schematic illustration showing the construction of the plasmid pKRCACO-A by the insertion of the coffee fruit-expressed ACC oxidase cDNA in the inverted, antisense orientation into a pKR1 transformation vector.

In another embodiment of the invention, the sequences corresponding to DNA that codes on expression for ACC oxidase were inserted into the plasmid in an inverted orientation adjacent to a cauliflower mosaic virus 35S promoter to form the DNA construct "pKRCACO-A" illustrated in FIG. 7. RNA transcribed therefrom is complementary (antisense) to all or part of the mRNA that encodes the amino acid sequence of coffee fruit-expressed ACC oxidase.

Figure 8:
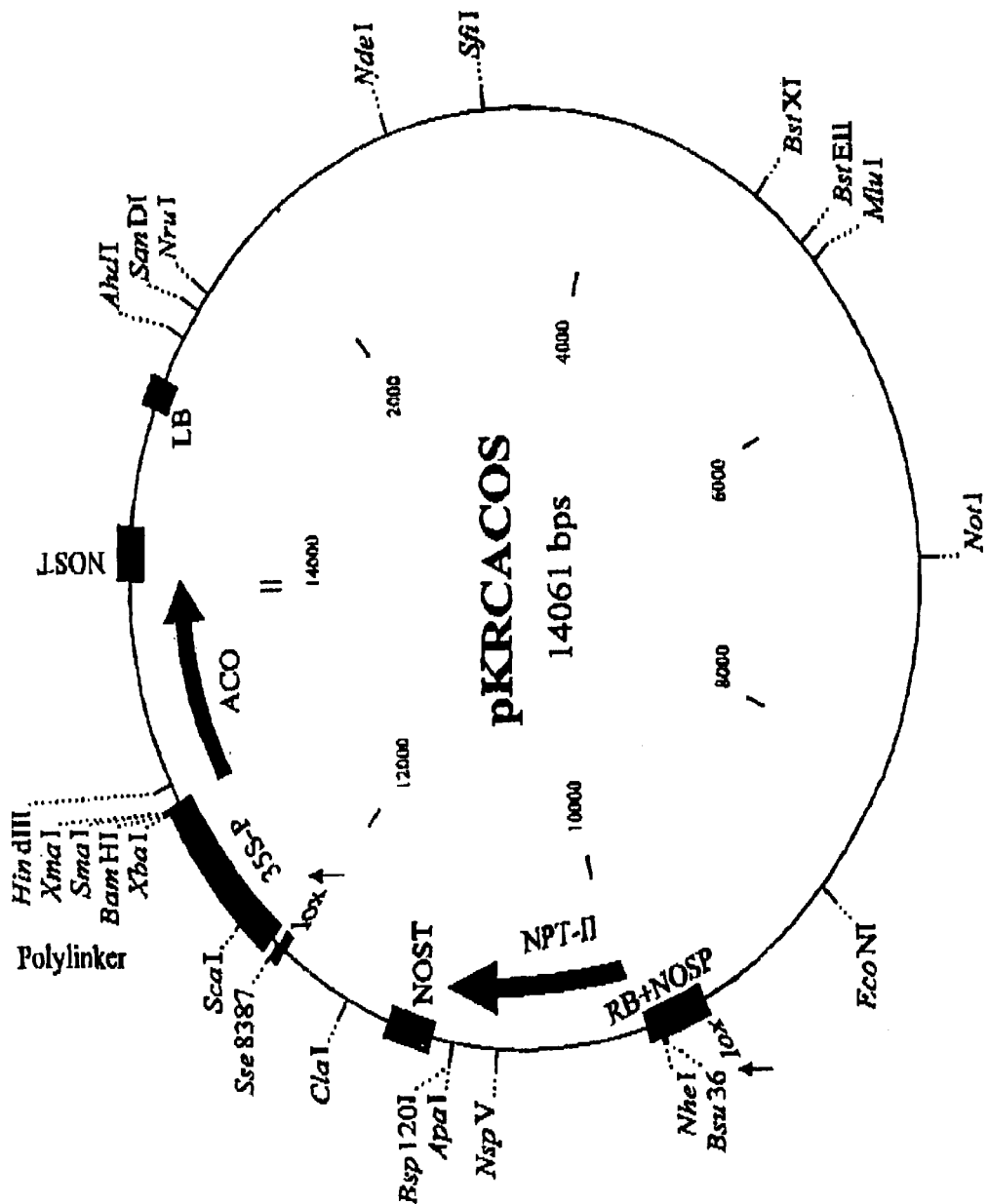
FIG. 8 is a schematic illustration showing the construction of the plasmid pKRCACO-SA by the insertion of the coffee fruit-expressed ACC oxidase cDNA in the sense orientation into a pKR1 transformation vector.

In another embodiment of the invention, the sequences corresponding to the DNA coding on expression for coffee fruit-expressed ACC oxidase were inserted into the plasmid in a sense orientation adjacent to the cauliflower mosaic virus 35S promoter to form the DNA construct "pKRCACO-S", illustrated in FIG. 8. RNA transcribed therefrom has substantially the same base sequence as all or part of the mRNA that encodes the amino acid sequence of coffee fruit-expressed ACC oxidase.

EXAMPLE 1

Expression of the Coffee ACC Synthase and ACC Oxidase Genes During Fruit Ripening a) Plant Tissue Coffee (*Coffea arabica* L.) of Guatemalan was used. Fruits at various stages of maturity were harvested from trees grown either at the University of Hawaii Waimanalo Research Station or at the Kunia Research Station of the Hawaii Agricultural Research Center, Oahu, Hi. Fruits were grouped into seven developmental stages on the basis of skin color and maturity: (1) immature green, (2) mature green, (3) yellow, (4) yellow-red, (5) 70% red, (6) 100% red, and (7) dark red. After making a transverse cut at the proximal end, each fruit from yellow stage through dark red was squeezed firmly until the bean was ejected from inside the fruit. Following the removal of the bean, the skin with remaining mesocarp tissue was quickly submerged into liquid $N_2$ and stored at −80° C. In younger stages, where beans could not be removed in this manner, skin and mesocarp were chipped from beans with a razor blade and immediately frozen in liquid $N_2$. A portion of the frozen tissue was ground into fine powder w with pieces of dry ice in a pre-cooled coffee mill (Salton Model GC-5, Salton Maxam Housewares, IL). The powder was either immediately used for RNA extraction or refrozen in liquid $N_2$.and stored at −80° C. for later use.

b) RNA Isolation

Total RNA was isolated using a modification of the previously published method of Levi et al. [*HortScience* 27, 1316–1318 (1992)]. Frozen coffee powder (2.0 g) was mixed with 30 ml homogenization buffer (200 mM tris:HCl, pH 8.5), 1.5% (w/v) sodium dodecylsulfate (SDS), 300 mM LiCl, 10 mM $Na_2EDTA$, 1.5% (w/v) sodium deoxycholate and 1.5% Nonidet P-40) containing 0.5 mM thiourea, 10 mM dithiothreitol (DTT), 75 mM 2-mercaptoethanol and 2% (w/v) molecular weight 36,000 polyvinylpyrrolidone (PVP), and homogenized with a Polytron® (Techmar, Ohio). Low temperature was maintained during homogenization by placing the contents in ice. Thirty ml of chloroform was added to the homogenate and stirring was continued for 1 minute. While stirring, 7.5 ml ethanol was added slowly to the homogenate, followed by an additional 30 ml of chloroform. Mixing was continued for 30 seconds after the chloroform was added for the second time. The homogenate was transferred to two 50 ml polypropylene centrifuge tubes and centrifuged for 15 minutes at 2500×g. The upper aqueous phase was transferred to a new centrifuge tube, mixed with 0.1 volume of 3M NaCl followed by 2×volume of ethanol, and stored at −20° C. for 1 hour. The RNA was then centrifuged, washed and resuspended in TE (10 mM tris:HCl, 1 mM EDTA, pH 8.0), as described by Levi et al. (1992, above).

c) Analysis of RNA Expression

Total RNA (20 μg) isolated from fruit at different stages of development was fractionated in 1% agarose-formaldehyde gel, as described by Fourney et al. [*Focus* 10, 5–7 (1988)]. Separate, but identical gels were prepared for ACC synthase and ACC oxidase blots. After fractionation, the RNA was transferred to nylon filters (MSI Micron Separation), as described by Fourney et al. (1988, above). Unless specified otherwise, the restriction enzymes and buffers used were from Promega Corporation (WI). An approximately 1900 bp fragment of ACC synthase cDNA was excised from pBlueScript SK vector with SmaI/BSrSI. The preparation of this vector containing the ACC synthase cDNA fragment is described below. The excision was performed in two steps. First, plasmid DNA (5 μg) was mixed with 10 μl 10×Multi-Core™ buffer [250 mM tris-acetate (pH 7.5), 1 M potassium acetate, 100 mM magnesium acetate, 10 mM DTT] and sterile water to 98 μl. After adding 1 μl SmaI (10 U/μl), the contents were incubated at 37° C. for 1 hour. In the second step, 1 μl BSrSI (10 U/μl) was added to the reaction mix and incubated at 65° C. for 1 hour.

An approximately 1100 bp ACC oxidase fragment was excised from pBlueScript SK vector with BamHI/BglII. The digestion was performed in 100 μl volume with 5 μg plasmid DNA, 10 μl of 10×buffer B [60 mM tris:HCl (pH 7.5), 60 mM $MgCl_2$, 500 mM NaCl and 10 mM DTT], 1 μl of BamHI (10 U/μl) and 1 μl of BglII (10 U/μl). The reaction mix was incubated for 1 hour at 37° C. for complete digestion.

After both ACC synthase and ACC oxidase cDNAs were excised from their respective plasmids, the fragments were separated by electrophoresis using 0.8% low melting agarose gel (SeaPlaque® agarose, FMC Bioproducts, ME) in 1×TBE buffer. Each fragment was excised from the gel and purified before using as a template for random labeled probe synthesis. Random labeled DNA probes were prepared using 50 ng of ACC synthase or ACC oxidase cDNA using the "Ready-To-Go" DNA labeling beads (Pharmacia Biotech, NJ) and 5 μL of 3000 Ci/mmol [α-$^{32}$P]dCTP] (NEN Life Science, MA).

Each northern blot was prehybridized for 30 minutes in 50 ml prehybridization buffer (50% formamide, 6×saline-sodium phosphate-EDTA (SSPE), 5×Denhardt's solution, 0.5% SDS and 100 μg/ml fragmented herring sperm DNA). Hybridization was performed in 5 ml of fresh prehybridization buffer at 42° C. After an overnight hybridization, the blots were washed as follows: one wash in 2×saline-sodium citrate (SSC, 1×SSC contains 150 mM NaCl and 15 mM sodium citrate), 0.5% SDS at room temperature; one wash in 2×SSC, 0.1% SDS at 50° C.; one wash in 0.1×SSC, 0.5% SDS at 50° C.; and two washes in 0.1×SSC, 0.1% SDS at 65° C. The filters blots autoradiographed in Fuji X-ray film and DuPont Cronex Lighting Plus intensifying screens.

d) Level of ACC Synthase and ACC Oxidase mRNA Present in Coffee Fruit during Ripening The level of ACC synthase and ACC oxidase mRNA present in coffee fruit during ripening is illustrated in FIG. 9. The upper panel in FIG. 9 shows expression of the ACC synthase gene during the ripening of coffee fruit. A small amount of ACC synthase mRNA is detected even in the young fruit, but the level of the ACC synthase mRNA increases rapidly as the fruits mature and reaches its peak at the yellow-red stage. The level of ACC synthase expression declines subsequently, but it remains at a higher level compared to the yellow or other younger stages.

Expression of ACC oxidase mRNA is illustrated in FIG. 9, lower panel, and appears to be similar to that of the ACC synthase, except that the levels of expression of the ACC oxidase mRNA are much higher. ACC oxidase mRNA expression peaks at yellow-red stage and begins to decline thereafter.

The rise in the expression of both ACC synthase and ACC oxidase mRNA during fruit ripening in coffee is consistent with the pattern observed in other climacteric fruit ripening.

EXAMPLE 2

Isolation of Coffee Fruit-Specific ACC Synthase cDNA a) Isolation of mRNA

Total RNA was isolated from 66 g of pericarp and mesocarp tissue from several different developmental stages of coffee fruit (*C. arabica* L. cv Guatemalan) using the method of Levi et. al., [*Hort Science* 27(12):1316–1318 (1992)]. Frozen coffee fruit pericarp and mesocarp tissue was powdered by grinding for about 2 minutes in a domestic coffee mill (Salton Model GC-5; Salton Maxam Housewares Group, Mt. Prospect, Ill.) with a small piece of dry ice. The powdered fruit tissue was added to 200 mL of 200 mM tris [hydroxymethyl]aminomethane hydrochloride (tris:HCl) (pH 8.5), 1.5% SDS, 300 mM LiCl, 10 mM disodium ethylenediaminetetraacetic acid ($Na_2EDTA$), 1.5% sodium deoxycholate (w:v), 1.5% Nonidet P-40 (Sigma Chemical Co.) (v:v), 0.5 mM thiourea, 1 mM aurintricarboxylic acid, 10 mM dithiothreitol (DTT), 75 mM β-mercaptoethanol, 2% polyvinylpyrrolidone (PVP) and 2% polyvinylpolypyrrolidone (PVP) and homogenized using a Polytron tissue homogenizer (Tekmar, Cincinnati, Ohio). After 2 minutes of homogenization, 200 mL of chloroform was added and homogenization continued for a further 3 minutes. The homogenate was transferred to 250 mL centrifuge bottles (Nalgene) and centrifuged for 15 minutes at 2,500×g. The upper aqueous phase was removed and mixed with 12 mL of 5 M NaCl, equally divided into two centrifuge bottles, and 150 mL of ethanol was added to each bottle. The mixture was stored at −20° C. overnight. The RNA was collected by centrifugation at 4,000×g for 15 minutes at 4° C. The RNA was dissolved in 50 mL TE1 (50 mM tris-HCl [pH 8.0], 10 mM $Na_2EDTA$) and clarified by centrifugation at 12,000×g for 10 minutes at 4° C. The supernatant was transferred to a new centrifuge bottle and 3 mL of 5 M NaCl and 30 mL of isopropanol were added. The to contents were mixed and stored at −20° C. overnight. The RNA was collected by centrifugation at 14,000×g for 10 minutes. The RNA was washed with 20 mL of 70% ice-cold ethanol and collected by centrifugation as before. After drying under vacuum for 10 minutes, the RNA was resuspended in 50 mL of TE1 buffer and 10 mL of 12 M LiCl was added. The solution was incubated at 4° C. for 48 hours and the RNA was collected by centrifugation at 14,000×g for 10 minutes and resuspended in 30 mL TE1 buffer. After the addition of 15 mL of 5 M potassium acetate, the RNA was incubated overnight at 0° C., recovered by centrifugation at 14,000×g for 10 minutes and suspended in 50 mL TE1 buffer. Three mL of 5 M NaCl and 110 mL of 95% ethanol were added and the RNA was incubated at −20° C. overnight. The RNA was recovered by centrifugation at 14,000×g for 10 minutes, washed with 20 mL of 70% ice-cold ethanol, recovered by centrifugation as above, dried under vacuum for 10 minutes and resuspended in 600 μL of TE1 buffer. The RNA was transferred into a microcentrifuge tube and centrifuged at 14,000 rpm for 30 minutes at 4° C. after which 300 μL was removed to each of two new microcentrifuge tubes. The original centrifuged tube was rinsed with an additional 300 μL of TE1 buffer. Eighteen μL of 5 M NaCl and 636 μL of 100% ethanol were added to each of the three tubes. After mixing by inverting, the tubes were stored overnight at −20° C. The RNA was collected by centrifugation at 14,000 rpm for 30 minutes and washed with 1 mL of 70% ice-cold ethanol. After centrifugation and drying as above, the RNA was resuspended in 400 μL sterile $H_2O$. A total of 1.04 mg total RNA was obtained.

Messenger RNA (poly $A^+$ RNA) was isolated using the PolyATtract® mRNA Isolation System IV (Promega Corporation, Madison, Wis.). A total of two isolations were done as follows. For each isolation, 0.48 mg total RNA was dissolved in 800 μL of RNase-free water. After heating at 65° C. for 10 minutes, 3 μL of 50 pmole/mL biotinylated oligo(dT) and 20.7 μL of 20×SSC were added and the mixture was allowed to slowly cool to room temperature over to a period of approximately 30 minutes. An aliquot of streptavidin paramagnetic particles (provided in the PolyATtrack® mRNA Isolation System IV) was washed 3 times in 0.5×SSC and resuspended in 0.1 mL of 0.5×SSC. The RNA solution containing the biotinylated oligo(dT) was added to the washed streptavidin paramagnetic particles. After a 10 minute incubation at room temperature, the paramagnetic particles containing the trapped mRNA were captured to the side of the tube using a magnet.

The supernatant was removed and the particles were washed four times with 0.3 mL of 0.1×SSC. The mRNA was removed from the biotinylated oligo(dT) particles by suspending in 200 μL RNase-free water. An additional elution was carried out by adding 150 μL of water sequentially to each of the two tubes. The elution fractions (550 μL) were pooled and centrifuged at 14,000 rpm in a microcentrifuge for 30 minutes at 4° C. The supernatant was divided into two microcentrifuge tubes and, after the addition of ¹⁄₁₀th volume of 3 M NaCl and 600 μL of ethanol, the mRNA was recovered by incubating the tubes at −20° C. overnight, followed by centrifugation as above. The mRNA was washed once with 1 mL of ice-cold 70% ethanol, dried and resuspended in 20 μL sterile $H_2O$. One AL was added to 1 mL of water and a spectrum was obtained from 230 nm through 330 nm in a Shimadzu UV 160U spectrophotometer. Approximately 6 kg of mRNA was recovered from 1.04 mg of total RNA.

b) Construction of a cDNA Library

First and second strand cDNA was synthesized using the ZAP-cDNA synthesis kit (Stratagene, La Jolla, Calif.). Six micrograms of mRNA in 20 μL of water were incubated at 65° C. for 5 minutes. Two microliters of 100 mM methyl mercury were added and incubation was continued at room temperature for 10 minutes. Four microliters of 700 mM β-mercaptoethanol were added and the incubation was continued for an additional 5 minutes. To the denatured mRNA, 5 μL of 10×first strand buffer (provided in the kit), 5 μL of 100 mM DTT, 3 μL nucleotide mixture (10 mM each dATP, dGTP, dTTP and 5-methyl-dCTP), 2 μL of 1.4 μg/μL linker-primer:

5'-GAGAGAGAGAGAGAGAGAGAGAACTAGTCTCG-
AGTTTTTTTTTTTTTTTTTT-3 (SEQ. ID NO. 1)

One μL RNase block and 5 μL of water were added. The reaction was incubated at room temperature for 10 minutes to anneal the primer to the mRNA and then 3 μL of 20 U/μL M-MuLV reverse transcriptase were added. Five microliters of this reaction mixture were removed to a tube containing 0.5 μL (0.625 pmoles) of 800 Ci/mmole [α-$^{32}$P]dATP. Both reactions were incubated at 37° C. for 1 hour. The radioactively labeled reaction was frozen at −20° for later gel analysis. To the 45 μL main reaction, 40 μL of second strand buffer, 15 μL of 100 mM DTT, 6 μL of nucleotide mixture (10 mM dATP, dGTP, dTTP and 26 mM dCTP), 268.3 μL water and 2 μL (2.5 pmoles) of 800 Ci/mmol [α-$^{32}$P]dATP were added. After mixing, 4.5 μL of 1 U/μL RNase H and 19.2 μL of 5.2 U/μL E.coli DNA polymerase I were added and the reaction was incubated at 16° C. for 2.5 hours. The reaction was extracted with 400 μL of phenol:chloroform (1:1). The phases were separated by centrifugation in a microcentrifuge for 5 min and the aqueous phase removed and re-extracted with chloroform. The aqueous phase was recovered by centrifugation as before.

The double-stranded cDNA was precipitated by the addition of 33.3 μL of 3M sodium acetate (pH 5.2) and 867 μL of 100% ethanol and incubation overnight at −20° C. The cDNA was recovered by centrifugation at 14,000×g in a microcentrifuge at 4° C. for 60 minutes. The cDNA was washed with 1 mL of 80% ethanol, recovered by centrifugation at room temperature in a microcentrifuge at 14,000× g, dried under vacuum and dissolved in 45 μL of water. Three microliters of the resuspended double-stranded cDNA was removed and stored at −20° C. for later analysis by gel electrophoresis.

To the remaining 42 μL of the double-stranded cDNA, 5 μL of 10×Klenow buffer (buffer #3; supplied by Stratagene), 2.5 μL of 2.5 mM nucleotides (dCTP, dGTP, dATP and dTTP), and 0.5 μL of 5 U/μL E. coli DNA polymerase I Klenow fragment were added. After 30 minutes at 37° C., 50 μL of water were added and the reaction was extracted with an equal volume of phenol:chloroform (1:1) and then chloroform as described above. After the addition of 7 μL of 3M sodium acetate (pH 5.2) and 226 μL of 100% ethanol, the blunt-ended double-stranded cDNA was incubated on ice for 30 minutes and recovered by centrifuging at 14,000 rpm at 4° C. for 60 minutes in a microcentrifuge. The cDNA was washed with 300 μL of 70% ethanol, centrifuged and dried as before. Seven microliters of 0.4 μg/μL EcoRI linkers were added to the dried cDNA. The structure of the EcoRI linkers are:

5'-AATTCGGCACGAG-3' (SEQ. ID NO. 2)
3'-GCCGTGCTC-5'

After vortexing to resuspend the cDNA, 1 μL of 10×ligation buffer, 1 μL 10 mM ATP and 1 μL of 4 Weiss U/μL T4 DNA ligase were added and the reaction was incubated over night at 8° C. The ligase was inactivated by heating at 70° C. for 30 minutes. The 5' ends of the EcoRI linkers, that are now attached to the cDNA, were phosphorylated using polynucleotide kinase. One microliter of 10×buffer #3 of the ZAP-cDNA synthesis kit (Stratagene, La Jolla, Calif.), 2 μL of 10 mM ATP, 6 μL of water and 1 μL of 10 U/μL T4 polynucleotide kinase were added to the ligation reaction. After 30 minutes at 37° C. the kinase reaction was stopped by heating the reaction at 70° C. for 30 minutes. XhoI "sticky ends" were generated at the end of the cDNA corresponding to the 3' end of the mRNA by digestion of the XhoI site in the linker-primer. Twenty-eight μL of XhoI buffer and 3 μL of 40 U/μL XhoI were added to the cDNA and the reaction was incubated at 37° C. for 1.5 hours.

The cDNA, with EcoRI sticky ends at the 5' end and XhoI sticky ends at the 3' end (relative to the original mRNA), was size fractionated by passage through a Sephacryl S-400 spin column prepared as follows. Five μL of 10×STE [100 mM Tris (pH 7.0), 5 mM EDTA and 100 mM NaCl] were added to the cDNA and the cDNA was applied to the top of a 1 mL syringe containing Sephacryl S-400 (Pharmacia Biotech, Piscataway, N.J.). A 500 μL microcentrifuge tube was placed on the bottom of the syringe and the column was placed in a centrifuge tube and centrifuged at about 400×g for 2 minutes. Sixty μL of 1×STE were added to the top of the syringe, a new microcentrifuge tube was placed on the bottom of the column and the column was again centrifuged as before. This process was repeated until six fractions had been collected. About 10% of each fraction was electrophoresed on a 1% agarose gel to determine the size distribution of the cDNA in each fraction. The remainder of each fraction was extracted with an equal volume of phenol:chloroform and then chloroform as described above and precipitated by the addition of 2 volumes of 100% ethanol. After overnight incubation at −20° C. the cDNA was recovered by centrifugation in a microcentrifuge at 14,000 rpm for 60 minutes at 4° C. Each cDNA fraction was washed with 200 μL of 80% ethanol and dried as described above. cDNA fraction 1 was resuspended in 3 μL of sterile water, and cDNA fraction 2 was resuspended in 10.5 μL of sterile water. One-half μL of each of the two fractions was used to determine the quantity of DNA using the ethidium bromide plate detection method. Fractions 1 and 2, containing the largest cDNA molecules, were combined. The 12.5 mL combined fractions contained approximately 100 ng of cDNA. This fraction was reduced to 2.5 μL in a Speed-Vac and stored on ice. cDNA fraction 3 was resuspended in 10.5 μL of sterile water, and saved at −20° C. for later use.

One hundred ng of cDNA from fraction 1 and 2 were ligated into 1 μg of Uni-ZAP (Stratagene, La Jolla, Calif.), a lambda ZAP vector that had been digested with EcoRI and XhoI. Fraction 1 and 2 cDNA (2.5 μL) were added to 0.5 μL of 10×ligation buffer, 0.5 μL 10 mM ATP, 1 μL of 1 μg/μL Uni-Zap XR vector and 0.5 μL of 4 Weiss U/μL T4 DNA ligase. The reaction was incubated at 8° C. for about 44 hours. A 1 μL aliquot of the ligation reaction was added to one aliquot of the 'Freeze-Thaw' extract from the Gigapack II Gold bacteriophage λ packaging kit (Stratagene, La Jolla, Calif.). Fifteen microliters of Sonic extract were added and the contents were gently mixed. The packaging was carried out at room temperature. After 2 hours, 500 μL of SM buffer and 20 μL of chloroform were added to each packaging reaction and the debris was removed by a short centrifugation in a microcentrifuge. The packaged phages were moved to a new microcentrifuge tube. Ten μL of chloroform were added and the packaged phages were stored at 4° C. until used. A titer of this primary library indicated the presence of 0.7×10$^6$ recombinant plaques.

c) Amplification of Primary Library

Six-hundred μL of E. coli XLI-Blue MRF' (Stratagene, La Jolla, Calif.), grown to a density of 0.5 at OD$_{600}$ and 32.5 μL of primary library stock were added to each of 16 tubes. After incubation at 37° C. for 15 min, 6.0 mL of 48° C. top agar (5 g/L NaCl, 2 g/L MgSO$_4$.7H$_2$O, 5 g/L yeast extract, 10 g/L NZ amine [pH 7.5], and 0.7% agarose) were added to each tube and the contents were plated on 150×15 mm NZY plates (5 g/L NaCl, 2 g/L MgSO$_4$.7H$_2$O, 5 g/L yeast extract, 10 μg/L NZ amine [pH 7.5], and 15 g/L Difco agar). The plates were incubated overnight at 37° C. and then overlayed with 10 mL of SM buffer and incubated for a further 8 hours at 4° C. with gentle shaking. The SM buffer was collected with a sterile pipette and stored in a sterile 250 mL centrifuge bottle. Each plate was rinsed with an additional 10 mL of SM buffer which were collected and added to the previous SM buffer. Chloroform, to a final concentration of 5%, was added and the phage solution was incubated at room temperature for to 15 minutes and then centrifuged at 2,000×g for 10 minutes to remove cell debris. The supernatant was recovered to a sterile polypropylene bottle and chloroform was added to a final concentration of 0.3%. The amplified library was stored at 4° C.

d) Plating of Amplified Library for Screening for Specific Genes

The amplified library was titered as described above. Approximately 50,000 recombinant plaques were added to 600 μL of *E. coli* XLI-Blue MRF' that were grown as described above. After 15 min at 37° C., 6.5 mL of 48° C. top agar were added and the cells were plated on 150×15 mm NZY plates. Four plates containing a total of 200,000 recombinant plaques were prepared and incubated at 37° C. overnight. The plates were then chilled for 4 hours at 4° C., then used for preparing plaque lifts as described below.

e) Identification and Construction of Oligonucleotides Homologous to Coffee ACC Synthase Genes In previous studies, described in our co-owned U.S. Pat. No. 5,767,376, we identified base sequences common to ACC synthase occurring in a variety of plants, referred to herein as consensus sequences. Based on these studies, we developed a set of three (3) fully degenerate primers for PCR amplification of regions of coffee first strand cDNA corresponding to consensus sequences. The sequence of the primers used is:

ACS167: 5'-GCCAAGCTTCCRTGRTARTCYTGRAA-3' (SEQ. ID NO. 3)

ACS289: 5'-TTYCARGAYTAYCAYGGHYT-3' (SEQ. ID NO. 4)

ACS885: 5'-CCHGGDARNCCYAWRTCTTT-3' (SEQ. ID NO. 5)

f) Reverse Transcriptase Reaction to Obtain First-strand Coffee cDNA

The reverse transcriptase reaction to obtain first-strand cDNA was performed in a final volume of 20 μL using the GeneAmp RNA PCR Core Kit (Perkin Elmer, Foster City, Calif.). First, 0.9 μg of coffee fruit mRNA in 3 μL water was mixed with 1 μL of 50 μM random hexamer and 6 μL of sterile water in a microcentrifuge tube and incubated at 65° C. for 5 minutes. The mixture was left at room temperature for 2 minutes and the liquid was recovered to the bottom of the tube by a brief centrifugation. To this mixture 2 μL PCR buffer II (from the above mentioned kit), 4 μL 25 mM MgCl$_2$, 2 μL 10 mM dNTP's, 1 μL RNAsin (20 u/μL), and 1 μL reverse transcriptase (50 u/μL) were added. The reaction was incubated at 42° C. for 1 hour after which the reverse transcriptase was heat inactivated in a 95° C. water bath for 5 minutes.

g) Polymerase Chain Reaction to Amplify Coffee ACC-synthase Gene

A polymerase chain reaction (PCR) (Saiki et al., 1988) was performed using the GeneAmp Kit described above in a 50 μL reaction containing 10 μL first-strand cDNA mix, 4 μL PCR buffer II, 1 μL 25 mM MgCl$_2$, 2.5 μL of 20 μM ACS167 primer (SBQ. ID NO. 3), 2.5 μL 20 μM ACS885 primer (SEQ. ID. NO. 5), 29.5 μL sterile H$_2$O, and 0.5 μL Taq DNA polymerase (5 u/μL). PCR conditions were 35 cycles of 94° C. for 1 minute, 44° C. for 1 minute, and 72° C. for 2 minutes. The product of the PCR reaction was analyzed by agarose gel electrophoresis using 1.5% Sea Plaque agarose (FMC BioProducts, Rockland, Me.) and Hae III-digested φX174 DNA (Promega Corporation, Madison, Wis.) as size markers. A single PCR product of approximately 650 bp was obtained.

h) Amplification of PCR Product with Different Primers

The 650 bp fragment obtained above was excised from the gel and placed in a 1.5 mL microcentrifuge tube. After the addition of 200 μL of sterile water, the 650 bp fragment was heated to 90° C. for 5 minutes, cooled to room temperature and centrifuged at 14,000 rpm for 5 minutes in a microcentrifuge. The supernatant containing the amplified DNA was removed and placed in a new sterile 1.5 mL microcentrifuge tube. A 25 μL PCR reaction was carried out using 0.4 μL of the previously amplified DNA as template, 2.5 μL 10×PCR buffer (10 mM Tris-HCl pH 9.0, 0.1% triton X-100), 2 μL 25 mM MgCl$_2$, 5 μL of 1 mM dNTPs, 1 μL of 20 μM ACS289 primer (SEQ. ID. NO. 5), 1 μL of 20 μM ACS885 primer (table 2), 12.8 μL H$_2$O, and 0.3 μL Taq DNA polymerase (5 u/μL) (Promega Corporation, Madison, Wis.). The PCR was performed using 35 cycles of 94° C for 1 minute, 45° C. for 1 minute, and 72° C. for 2 minutes. Five μL of this reaction was electrophoresed in a 1.5% agarose gel as described above. A single product of approximately 603 bp was observed. Eighty μL of sterile water, 10 μL of 3 M sodium acetate (pH 5.2), and 220 μL of 100% ethanol was added to the remainder of the reaction. After incubation at −20° C. overnight, the DNA was recovered by centrifugation at 4° C. for 30 minutes at 14,000 rpm. The DNA was washed with 400 μL of ice-cold 75% ethanol and resuspended in 25 μL of sterile water. The DNA concentration was determined to be 10 ng/μL using the ethidium bromide plate assay.

i) Labeling Coffee Fruit-Specific ACC Synthase DNA

A random primed probe was produced using the PCR-generated ACC synthase DNA and the Prime-a-Gene Kit (Promega Corporation, Madison, Wis.). Two and one-half μL of the DNA (25 ng) was added to 27.5 μL of sterile water and the DNA was denatured by boiling for 5 min. Ten μL of 5×labeling buffer, 2 μL of unlabeled dNTP's [20 μM each; dCTP, dGTP, dTTP], 2 μL 1 mg/mL acetylated BSA, 1 μL 5u/μL *E. Coli* DNA polymerase I Klenow fragment and 5 μL (50 μCi) of [α-$^{32}$P]dATP (3,000 Ci/mmole) (Dupont-NEN) were added to give a final volume of 50 μL. After 1 hr at room temperature, the reaction was terminated by the addition of 2 μL of 0.5 M Na$_2$EDTA and boiling for 2 min.

j) Screening of Amplified Library with the ACC Synthase-specific Probe

Plaque lifts of the four 150×15 mm NZY plates containing 50,000 recombinant clones each were prepared. Four 132 mm Magna nylon transfer membranes (Micron Separations, Incorporated, Westborough, Mass.) were wetted by placing them on chromatography paper saturated with 5×SSC buffer for approximately 10 sec. The membranes were placed on the plates containing the recombinant plaques for 5 min, removed and incubated, phage containing side up, for 2 min on chromatography paper saturated with 0.5 M NaOH and 1.5 M NaCl. The membranes were then neutralized by transferring onto chromatography paper saturated with 0.5 M tris-HCl (pH 8.0) and 1.5 M NaCl, for 5 min. After a brief 20 sec treatment on chromatography sheets saturated with 2×SCC containing 0.2 M tris-HCl (pH 7.5), the filters were blotted dry. After 1 hour of air drying, DNA was cross-linked to the membranes by treatment with 12,000 μJoules of a 260 nm UV light in a UV Stratalinker 1800 (Stratagene, La Jolla, Calif.).

The four membranes were pre-hybridized at 65° C. for 2 hours in 100 mL 6×SSPE (52.2 g/L NaCl, 8.3 g/L NaH$_2$PO$_4$.H$_2$O, 2.2 g/L Na$_2$EDTA, [pH 7.4]), 5×Denhardt's solution (1 g/L Ficoll, 1 g/L polyvinylpyrrolidone, 1 g/L BSA [pentax fraction V]), 0.5% SDS and 100 µg/mL denatured herring sperm DNA in a Hybaid Mark II hybridization oven (National Labnet Company, Woodbridge, N.J.) using HB-OV-BL bottles.

Hybridization was carried out at 65° C. for 12 hours in 10 mL of 6×SSPE containing 0.5% SDS, 100 µg/mL denatured herring sperm DNA, and 52 µL of the random primed probe described above. At the end of the hybridization period the hybridization solution was removed and the membranes were briefly washed with 100 mL of 2×SSC containing 0.5 % SDS at 65° C. They were then washed for an additional 30 min with the same amount of fresh buffer again at 65° C. The membranes were washed twice more for 30 min at 65° C. with 100 mL of 0.2×SSC containing 0.5% SDS, wrapped in a cellophane envelope and exposed to pre-flashed Fuji $RX_{GCU}$ X-ray film at −70° C. for 24 hours. Ten positive clones were obtained. The region of the original plates corresponding to the identified plaques were removed and placed in 1 mL of SM buffer containing 20 µL chloroform. Of these ten, 5 were re-plated at lower densities and rescreened as above to obtain individual plaques.

k) Characterization of Coffee-Fruit ACC Synthase cDNA Clones

The size of the putative coffee ACC synthase cDNA clones was determined by polymerase chain reaction using primers homologous to a portion of the T3 and T7 promoters present in the cloning vector and flanking the cDNA insertion site. The sequence of the primers are:

T3: 5'-TAATACGACTCACTATAGGG-3' (SEQ. ID NO. 6)

T7: 5'-AATTAACCCTCACTAAAGGG-3' (SEQ. ID NO. 7)

The conditions for PCR were as described above except that the temperature cycle was 95° C. for 1 min., 50° C. for 1 min. and 72° C. for 2 min. Analysis was by agarose gel electrophoresis as before.

The three largest clones were recovered as phagemids by in vivo excision. Two hundred µL of phage stock from a single plaque was mixed with 200 µL of E. coli XL1-Blue MRF' grown to a density at $OD_{600}$ of 1.0. One µL of ExAssist (Stratagene, La Jolla, Calif.) helper phage (>1×10$^6$ pfu/µL) was added and the tubes were incubated at 37° C. for 15 min. Three mL of sterile LB broth were added and they were incubated for 3 hours at 37° C. with shaking. After heating at 70° C. for 20 min and centrifugation at 1000×g for 15 min, 1 mL of the supernatant, containing the excised pBluescript phagemid packaged as filamentous phage particles, was transferred to a sterile 1.5 mL microcentrifuge tube and stored at 4° C. Phagemids were recovered by adding 25 µL of the stock solution to 200 µL of E. coli Solar cells (Stratagene, La Jolla, Calif.) grown to a density of 1 when measured at $OD_{600}$. After incubation at 37° C. for 15 min, 200 µL of the cell mixture was plated on 100×15 mm NZY agar plates containing 50 µg/mL ampicillin. The plates were incubated overnight at 37° C. Individual colonies were picked into 10 mL of LB broth containing 50 µg/mL ampicillin and grown overnight in a 37° C. shaking incubator. The cells were concentrated in a 1.5 mL sterile microcentrifuge tube by repeated centrifugation and the phagemid DNA was purified using the plasmid mini kit from QIAGEN. The bacterial pellets were washed with water and resuspended in 0.3 mL of buffer P1. Next, 0.3 mL of alkaline lysis buffer P2 was added, mixed gently, and incubated for less than 5 min at room temperature. Following the addition of 0.3 mL of chilled buffer P3 and mixing by inverting the tubes 6 times, the extracts were incubated on ice for 10 min and centrifuged at 14,000 rpm for 15 min in a microcentrifuge. The supernatants were removed and applied to QIAGEN-tip 20 columns that had been previously equilibrated with 1 mL of QDT buffer. The extracts were allowed to enter the resin of the columns by gravity flow. Once the flow had stopped, the columns were washed 4 times with 1 mL buffer QC. The DNAs were eluted by washing the QIAGEN-tip 20 columns with 0.8 mL buffer QF which was collected into 1.5 mL microcentrifuge tubes. The DNA was precipitated by the addition of 0.7 volumes (560 µL) of isopropanol. The tubes were immediately centrifuged at 14,000 rpm for 30 min and the supernatant carefully removed. The pellets, containing the DNA, were washed with 1 mL of ice-cold 70% ethanol, centrifuged as above, and air dried for 5 min. The DNA was resuspended in 50 µL sterile $H_2O$. The concentration of DNA from one plasmid isolation was 0.1 µg/µL by fluormetric analysis.

Sequencing reactions were performed by mixing 8 µL of phagemid DNA (0.8 µg) with 4 µL of either T3 or T7 sequencing primers (0.8 pmol/µL). Automated DNA sequencing was carried out on these samples at the University of Hawaii Biotechnology Service Center. About 350 bp of sequence from both the 5' and the 3' end of the cDNA was obtained. New sequencing primers were synthesized based on sequences near the end of the previous sequences and used in the same manner to complete the sequence of both strands of the cDNA. The complete sequence of the coffee fruit-expressed ACC synthase cDNA is given in FIG. 1. The deduced amino acid sequence of the coffee fruit-expressed ACC synthase is given in FIG. 2. The sequence of the coffee ACC synthase cDNA clone and deduced protein was compared with other ACC synthase genes present in GenBank. The cDNA isolated from coffee fruit shows from 68.3% to 58.1% identity to other ACC synthases present in GenBank. And, the protein sequence deduced from this cDNA shows from 67.9% to 50.5% identity to other ACC synthases. However, this cDNA is unique in that no other sequence greater than 1500 bp showed greater than 68.3% identity to it.

EXAMPLE 3

Isolation of Coffee Fruit-Specific ACC Oxidase a) Synthesis of ACC Oxidase Specific Oligonucleotide Primers The isolation of total RNA, mRNA, and the synthesis of coffee fruit-specific cDNA was as described above.

Twelve ACC oxidase sequences, obtained from GenBank, were aligned using the Pileup program of GCG (Genetics Computer Group, Madison, Wis.). A region approximately 1000 bp from the translation start codon was found to be conserved and a degenerate oligonucleotide primer

5'-TCATGCKKCRAKIGGTTC-3'(SEQ. ID NO. 8)

corresponding to this region was synthesized. Inosine (I) was placed at positions showing no sequence conservation, since position could be any of A, T, G or C. Positions showing two-fold ambiguity were prepared with mixed residues (T/G or A/G). We also prepared a second primer homologous to a region of the papaya fruit-expressed ACC oxidase cDNA that had been previously cloned in our laboratory and situated approximately 372 bp from the translational start codon:

5'-GACACTGTGGAGAGGCTGAC-3'(SEQ. ID NO. 9)

The two primers were used in a PCR reaction to amplify a portion of the coffee fruit-expressed ACC oxidase. The PCR contained 0.2 µL (10 ng) cDNA fraction 3 (described in Example 2), 5 µL 10×PCR buffer, 3 µL 25 mM $MgCl_2$, 1 µL of each of the four 10 mM dNTPs, 1 µL of a 20 µM solution of each primer, 0.3 µL Taq DNA polymerase (Promega Corporation, Madison, Wis.) and 38.5 µL water. PCR conditions were 35 cycles of 94° C. for 1 min, 50° C. 1 min, and 72° C. for 1 min. A 5 min incubation at 72° C. was carried out after the last cycle. A 20 µL aliquot of the product was electrophoresed in a 1.5% agarose gel as described previously and revealed an approximately 800 bp product. The DNA was excised from the gel and mixed with 200 µL of sterile water in a 1.5 mL microcentrifuge tube. After boiling for 5 min, 2 µL was used as a template in a 50 µL PCR reaction as above using the same primers. Gel electrophoresis performed as described above using 20 µL of the PCR reaction indicated the presence of a single 800 bp product. To the remaining 30 µL of the PCR reaction 20 µL chloroform and 100 µL water was added. The contents were mixed and centrifuged for 2 minutes at 14,000 rpm in a microcentrifuge. The upper aqueous phase containing the DNA was removed to a clean microcentrifuge tube. A portion of this DNA was radioactively labeled by random primed synthesis as described above.

b) Screening of Amplified Library with Random Primed Probe

The amplified coffee-fruit cDNA described in Example 2 was used to prepare four 150×10 mm NZY plates as previously described. Pre-hybridization, hybridization and recovery of clones was as previously described except that the ACC oxidase sequence obtained by PCR was used as the probe.

c) Characterization of Coffee-Fruit ACC-oxidase cDNA Clones

The size of the coffee ACC-oxidase cDNA clones was determined by polymerase chain reaction using primers homologous to the T3 and T7 promoters as described in Example 2.

The sequence of the largest coffee ACC oxidase cDNA clone was obtained as described in Example 2 and compared with ACC oxidase genes present in GenBank. FIG. 4 gives the cDNA sequence of the coffee fruit-specific ACC oxidase. FIG. 3 gives the deduced amino acid sequence of this protein. The cDNA was determined to encode ACC oxidase because it is from 50.4% to 82.5% identical to other ACC oxidase nucleic acid sequences present in GenBank. Also, the deduced protein sequence is from 32.5% to 86.5% identical to other ACC oxidases.

EXAMPLE 4 a) Construction of Vectors for the Expression of Anti-sense ACC Synthase and ACC Oxidase Transcripts The ACC synthase and ACC oxidase cDNAs can be used to modify ethylene content in coffee by, for example, anti-sense expression or co-suppression. An example of its use with the vector pKR1 is described. This is only an example and many other plant transformation vectors could be used in conjunction with the ACC synthase and ACC oxidase cDNAs. The vector, pKR1, was created by modification of pBI-121 (Clontech Laboratories), as follows:

Two 38-base pair synthetic sequences containing lox recognition sites for the cre site-specific recombinase were inserted surrounding the neomycin phosphotransferase II (NPT II) selectable marker gene of pBI-121. These lox sites allow for the removal of the NPT II gene from the construct after it is integrated into the plant genome [Dale and Ow, Proc. Natl. Acad.Sci. USA 88:10558 (1991)], but are not pertinent to the function of the ACC synthase and ACC oxidase cDNAs in antisense.

Three synthetic oligonucteotides were synthesized based on the loxP sequences defined by Dale and Ow (supra). The sequence of these oligonucleotides are:

loxA:
5'-AGCTATAACTTCGTATAGCATACATTATACG-AAGTTAT-3' (SEQ ID NO:14)

loxB:
5'-AGCTATAACTTCGTATAATGTATGCTATACG-AAGTTAT-3' (SEQ ID NO:15), and loxC:
5'-ATAACTTCGTATAGCATACATTATACGAAG-TTATAGCT-3' (SEQ ID NO:16).

loxB is the complementary strand to both loxA and loxC. When loxA and loxB were annealed they formed a double-stranded molecule with 4-base overhangs complementary to HindIII overhangs which allows insertion of the double-stranded sequence into a HindIII site such as that found after the NOS transcription termination sequence adjacent to the NPT II gene in pBI-121. Annealing of loxC with loxB produces a blunt-ended double-stranded DNA containing a lox recognition site.

Synthetic lox sites were inserted surrounding the NPT II gene of pBI-121 as follows. pBI-121 was digested with PmeI (New England Biolabs, Beverly, Mass.) at 37° C. for 2 hours in reaction buffer supplied by the manufacturer. pBI-121 has a single PmeI site just proximal to the NOS promoter that drives expression of the NPT II gene. A synthetic lox site was generated by annealing equimolar amounts of loxB and loxC by heating at 95 ° C., slowly cooling to room temperature and ligating into the PmeI-digested pBI-121. The 30 µL ligation reaction contained ligation buffer (New England Biolabs, Beverly, Mass.), 60 nmoles PmeI-digested pBI-121, 3 µL of a 1 µM stock solution of annealed loxB/loxC, 4 units PmeI and 4,000 units of high concentration T4 DNA ligase (New England Biolabs, Beverly, Mass.). Ligation was at 16° C. overnight. One to 4 µL of the ligation reaction were electroporated into E. coli XL1-Blue cells (Stratagene) and plated onto LB plates containing 50 µg/mL kanamycin, 50 µL of 20 mg/mL X-gal and 10 µL of 100 mM IPTG. White colonies were picked to fresh LB-kanamycin master plates.

Colonies containing the lox site were identified by colony hybridization. The master plates were grown for 4 hours at 37° C. and blotted to nylon membranes (MSI). The membranes were placed on fresh LB-kanamycin plates and grown at 37° C. overnight. The membranes were floated on 0.5 M NaOH for 10 minutes, neutralized by floating on 0.5 M Tris-HCl (pH 8.0) containing 0.5 M NaCl for 2 minutes and rinsed in 2×SSC.

The membranes were pre-hybridized in 20 mL of 6×SSPE, 5×Denhardt's solution, 0.5% SDS and 100 µg/mL fragmented herring sperm DNA at 55° C. for 3 hours. The pre-hybridization solution was replaced with 10 mL of fresh solution containing $8.4 \times 10^6$ cpm of loxC labeled at the 5' end with [$^{32}$P] using T4 polynucleotide kinase. The 50 µL labeling reaction contained 50 pmoles of loxC, polynucleotide kinase reaction buffer (Promega), 15 µL of 3,000 Ci/mmol [–$^{32}$P] ATP (DuPont-NEN) and 20 units T4 polynucleotide kinase (Promega). The reaction was incubated at 37° C. for 10 minutes and the product was separated from the unincorporated ATP using a Sephadex G-25 spin column. Hybridization was at 55 ° C. overnight. The filters were washed at 55° C. twice in 100 mL of 2×SSC containing 0.5% SDS, once with 100 mL of 1×SSC containing 0.5% SDS and autoradiographed as described previously. Several colonies were found to hybridize intensely and were selected for further characterization. Plasmid DNA was extracted using the Magic Minipreps DNA Purification System® (Promega) and digested with PmeI as described above. Plasmids containing the lox site will no longer have a PmeI site. Plasmids that were resistant to digestion by PmeI were further analyzed by automated DNA sequencing at the University of Hawaii Biotechnology Service Center, to confirm insertion of a lox site.

A plasmid containing the lox site in the desired orientation was digested with HindIII mixed with loxA/loxB heteroduplex that contains HindIII sticky-ends but not a complete HindIII restriction site, annealed as described above and ligated. The ligation reaction contained 2.5 µg of HindIII-digested plasmid, 1.25 pmoles of loxA/loxB, ligation buffer (Promega), 6 units of T4 DNA ligase (Promega), 1.25 units of HindIII (Promega) in a final volume of 30 µL. The reaction was incubated at room temperature for 1 hour, heated at 80° C. for 10 min and introduced into E. coli XL1-Blue cells by electroporation (Stratagene). Random plasmids were screened for loss of the HindIII site by digestion with HindIII as above. Final confirmation of this plasmid structure, designated pKR1, was obtained by DNA sequencing as described above.

pKR1 was digested with SacI. The 173 µL reaction contained 10 µg pKR1, multicore buffer (Promega), and 20 units of SacI (Promega). After 1 hour at 37° C., 0.7 µL of 25 nM stocks of dATP, dCTP, dGTP and dTTP and 10 units of T4 DNA polymerase (Promega) were added. This reaction, which will make the SacI digestion products blunt-ended, was incubated at 15° C. for 30 minutes. After inactivation of the T4 DNA polymerase by incubation at 75° C. for 15 minutes, 24 units of SmaI were added and the reaction was incubated at room temperature for two hours. The reaction was stopped by heating at 80° C. for 15 minutes. The DNA was precipitated by the addition of 17 µL of 3 M sodium acetate and 375 µL of 100% ethanol. After 1 hour at −70° C. the DNA was recovered by centrifugation in a microcentrifuge at full-speed for 20 min at 4° C. The DNA was washed with 70% ethanol, dried under vacuum and dissolved in 88 µL water. Ten µL of 10×calf intestinal alkaline phosphatase buffer (Promega) and 20 units of calf intestinal alkaline phosphatase were added and the reaction was incubated at 37° C. for 2 hours. The reaction was stopped by the addition of 4 µL of 0.5 M EDTA and heating at 75° C. for 10 minutes. The sample was extracted with an equal volume of water saturated phenol, then with an equal volume of phenol:chloroform (1:1) and finally with chloroform. The DNA was recovered by precipitation after adding 0.1 volume of 3 M sodium acetate and 2.5 volumes of 100% ethanol.

The coffee ACC synthase and ACC oxidase cDNA inserts were released from original plasmids, pACS and pACO, using restriction enzymes as follows. Ten µg of pACS plasmid was digested in 100 µL containing 10 µL of 10×Multicore buffer (Promega), 40 units SmaI. After incubation at 25° C. overnight, 40 units of BsrSI were added and the reaction was continued at 67° C. After 2 hours at 67° C., the reaction tube was cooled in ice for 10 min followed by incubation at 37° C. The reaction mix was supplemented with 1 µL of 10 mM dNTP (dATP, dCTP, dGTP and dTTP), 1 µL of 1 mg/mL acetylated BSA and 15 units of T4 DNA polymerase (Promega). The reaction was incubated at 37° C. for 5 minutes to make the DNA blunt-ended. After inactivation of the T4 DNA polymerase by incubation at 75° C. for 30 minutes, the volume was reduced to 50 µL in a Speed-Vac®. The digestion products were separated by electrophoresis on a 1% SeaPlaque agarose gel. The 1.6 kb coffee ACC synthase cDNA was excised from the agarose gel and the cDNA insert recovered by digestion of the agarose with 1.12 units of Agar ace (Promega). After incubation at 45° C. for 30 min, the cDNA was precipitated by adding 24 µL of 3 M sodium acetate (pH 5.2) and 600 µL of 95% ethanol.

The ethanol-precipitated cDNA was centrifuged for 30 min at room temperature, the supernatant discarded, and the pellet was washed with ice-cold 70% ethanol and centrifuged as above. The pellet was dissolved in 100 µL water and subsequently used in the blunt-end ligation into the pKR1 vector.

The ACC oxidase cDNA insert was prepared in a similar manner described for the pACS cDNAs above. Ten µg of pACO plasmid was digested in 100 µL containing 10 µL of 10×buffer C (Promega), 1 µL of 1 mg/mL acetylated BSA, 30 units of Bali and 30 units of bamboo. After incubation at 37° C. for 2 hours, the reaction mix was supplemented with 1 µL of 10 mM dNTP (dATP, dCTP, dGTP and dTTP) and 15 units of T4 DNA polymerase (Promega). The reaction was incubated at 37° C. for 5 minutes to generate blunt-ends. After inactivation of the T4 DNA polymerase by incubation at 75 ° C. for 30 minutes, the volume was reduced to 50 µL in a Speed-Vac®. The digestion products were separated by electrophoresis on a 1% SeaPlaque agarose gel. The 1 kb coffee ACC oxidase cDNA was excised from the agarose gel and the cDNA insert recovered by digestion of the agarose with 1.12 units of Agar ace (Promega). The purification of the cDNA insert from agarose was as described for the ACC synthase insert. The pellet was dissolved in 50 µL water and subsequently used in the blunt-end ligation into the pKR1 vector.

The purified ACC synthase and ACC oxidase inserts were ligated in pKR1 vector by mixing 500 ng of pKR1 vector (SmaI/SacI fragment blunt ended and phosphatased) and 150 ng of either ACC synthase or ACC oxidase insert in separate tubes. The volume of each vector/insert mixture was reduced to 8 µL using a Speed-Vac®. To each of the vector/insert tubes, 1 µL of 10×ligase buffer (Promega) and 1 µL of T4 DNA ligase (10 units) were added. The contents were incubated at 8° C. for 48 hours.

One µL of each ligation product was mixed with 40 µL of XL-1 Blue cells (previously prepared for electroporation and stored at −70° C.) and electroporated using "Electro Cell Manipulator 600" (ECM 600, BTX Inc., CA) at 2.35 KV for 5 mseC. Immediately after electroporation, 1 mL of LB buffer was added to each tube and incubated in a rotary shaker for 1 hour at 250 RPM. After the incubation, the bacteria were precipitated by centrifugation at 1400 RPM for 2 min and the volume was reduced to 100 µL. Fifty µL of the mixture was plated into LB plates containing 40 µg/mL kanamycin and incubated overnight at 37° C. Colonies growing in kanamycin plates were further screened to identify clones that included the ACC synthase or ACC oxidase inserts. Individual clones were harvested using sterile tooth picks and laid on fresh LB-kanamycin plates in a grid pattern. There were three plates for each cDNA insert (ACC synthase and ACC oxidase). After overnight growth in the grid, the bacteria were replica blotted in Magna nylon membranes (MSI, MA). The membranes were sequentially treated in 10% SDS for 5 min, 0.5 M NaOH and 1.5 M NaCl for 15 min, 0.5 M Tris-HCl and 1.5 M NaCl for 15 min, and 2×SSC and 0.2 M Tris-HCl for 5 min. The membranes were allowed to air dry and baked at 80° C. for 20 min and cross-linked by 120,000 µJoules of UV illumination (Strata Linker UV crosslinker 1800, Stratagene, CA).

The membranes were pre-hybridized for 2 hours in 6×SSPE, 5×Denhardt's solution, 0.5% SDS and 100 µg/mL herring sperm DNA at 65° C. Probes for ACC synthase and ACC oxidase were synthesized using Ready-to-Go DNA labeling beads (Pharmacia). Fifty ng of each cDNA insert was denatured by boiling in 45 µL water and quenched in ice. The 45 µL denatured DNA was mixed with Ready-to-Go DNA labeling beads and 5 μL of [$^{32}$-P] dCTP (3000 Ci/mmol) and incubated at 37° C. for 30 min. After the probe synthesis, the tubes were boiled in water for 4 min and quenched in ice. The pre-hybridization buffer was discarded and 10 mL of pre-heated hybridization buffer (6×SSPE, 0.5% SDS and 100 μg/mL herring sperm DNA) was put into each hybridization bottle followed by the addition of the denatured probe. Hybridization was performed overnight at 65° C.

The membranes were washed briefly with 2×SSC and 0.5% SDS. A second wash with the same buffer was performed for 30 min. The membranes were washed 2× with 0.2×SSC and 0.5×SDS. Each wash was for 30 min. The membranes were then autoradiographed. Five pKR1 clones with ACC synthase and 24 clones with ACC oxidase were identified upon developing the autoradiogram. The gene orientation in each clone was identified employing PCR, restriction digestion and sequencing the vector/insert junction. A pinch of bacterial colony from each of the 29 clones (5 ACC synthase and 24 ACC oxidase) were picked using toothpicks and suspended in 20 μL sterile Milli-Q water (cell dilution). The 25 μL PCR reactions contained 2 μL of the above cell dilutions, 0.5 μL of a 10 mM stock of each dATP, dCTP, dGTP and dTTP, 1.5 μL 25 mM MgCl$_2$, 2.5 μL 10×buffer (Promega), 1 μL each of three 20 μM primers given below, 0.3 μL 5 units/μL Taq DNA polymerase (Promega) and 16.2 μL sterile Milli-Q water. The primers used for ACC synthase clones were: 35S primer (5'-CCA CTA TCC TTC GCA AGA CC-3') (SEQ ID NO:17); ACSR$_7$ (5'-TTG CCA TCT TCG ACA AGA CT-3') (SEQ ID NO:18); and ACSL$_4$ (5'-CTG TTG TCA GCT GTG CTA-3') (SEQ ID NO:19). Likewise the primers used for ACC oxidase clones were: 35S primer; ACOR$_4$ (5'-GGA CTT CTG AGA TGT TGG AA-3') (SEQ ID NO:20); and ACOL$_1$ (5'-TGG TGG AGA GCA AGG AAT TG-3') (SEQ ID NO:21). The thermal cycling conditions were 10 minutes at 94 C.; 35 cycles of 1 minute at 94 C., 1 minute at 50 C., 1 minute at 72 C, and 5 minutes at 72 C. The expected sizes of the PCR products for pKR1/ACC synthase construct were 320 bp (35S and ACSR$_7$) for the sense orientation and 850 bp (35S and ACSL$_4$) for the antisense orientation. Similarly, the expected products for pKR1/ACC oxidase construct were 400 bp (35S and ACOR$_4$) for the sense orientation and 800 bp (35S and ACOL$_1$) for the antisense orientation. For both ACC synthase and ACC oxidase, one plasmid each with the cDNA in the sense and in the antisense direction were further analyzed by DNA sequencing of the junctions between the plasmid and cDNA to confirm the orientation. DNA sequencing was carried out as previously described. The binary vectors with ACC synthase gene in antisense orientation (designated pKRCACS-A), ACC synthase in sense orientation pKRCACS-S), ACC oxidase in antisense orientation (pKRCACO-A) and ACC oxidase in sense orientation (pKRCACO-S) are shown in FIGS. 5–8, respectively.

b) Electroporation of Agrobacteria with pKR1 Plasmid Containing the ACC Synthase (pKRCACS-S and pKRCACS-A) and ACC Oxidase (pKRCACO-S and pKRCACO-A) cDNAs Gene in Sense and Antisense Orientation Agrobacterium strain LBA 4404 was grown from a single colony to OD$_{600}$ in 100 mL YM liquid media (0.4 g/L Yeast extract, 10 g/L mannitol, 0.1 g/L NaCl, 0.2 g/L MgSO$_4$.7H$_2$O, 0.5 g/L K$_2$HPO$_4$, pH 7.5) in a rotary shaker at 29° C. for 48 hours. The cells were concentrated by centrifugation at 4000×g to 6×10$^{11}$ cells/mL. Electroporation was performed using the "Electro Cell Manipulator 600" (ECM 600, BTX Inc., CA). A 3.5 μL aliquot of either pKRCACS-A, pKRCACO-A, pKRCACS-S or pKRCACO-S plasmid solution containing 200 ng of DNA was mixed with 50 μL of concentrated Agrobacteria cells and transferred to a pre-cooled 2 mm gap cuvette (BTX Inc., CA) and a 5 ms pulse at 2.35 kV was applied. One mL of YM liquid media containing 50 μg/mL kanamycin was added to the electroporated cells and they were allowed to recover for 1 hour in a 29° C. shaker at 250 RPM. The cells were centrifuged at 4000×g and resuspended in 100 μL fresh YM liquid media. Transformed bacteria were selected on YM-agar plates (YM liquid media containing 15 g/L Bacto-agar) supplemented with 50 μg/mL kanamycin.

Confirmation of Agrobacterium transformation after incubation at 29° C. for 48 hours was obtained by picking 10 colonies from each transformation to fresh YM-agar/kanamycin plates on a marked grid. The presence and orientation of the ACC synthase and ACC oxidase gene insert was determined by PCR using the 35S primer in conduction with one of the internal gene-specific primers. A small amount of each colony was transferred to 20 μL sterile Milli-Q water using a sterile toothpick. PCR reactions were performed as described above using 2 μL of these cell suspensions as template DNA. For the ACC synthase sense orientation the 35S and ACSR$_7$ primers were used and produced a product of the expected size, 320 bp. The ACC synthase antisense primers 35S and ACSL$_4$ gave the expected product of 850 bp. Similarly, for the ACC oxidase sense orientation the 35S and ACOR$_4$ primers were used and produced a product of the expected size, 400 bp. The ACC oxidase antisense primers 35S and ACOL$_1$ gave the expected product of 800 bp. We selected one colony of each orientation for transformation of coffee leaf tissue.

c) Infection of Coffee Leaf Tissue with Agrobacteria Containing the pKRCACS-S, pKRCACO-S, pKRCACS-A and pKRCACO-A Plasmids Mature young coffee leaves from plagiotrophic shoots were sterilized in 30% Clorox for 30 minutes and rinsed three times in sterilized distilled water. Approximately 7 mm$^2$ pieces from the lamina between the midrib and the margin were excised and placed in MS liquid media (Murashige and Skoog, 1962) with an Agrobacterium slurry of 10 cells/mL and co-cultivated for three hours. The leaf tissue was blotted dry with sterilized paper towels and co-cultivated with the remaining Agrobacterium for three days on MS media solidified by the addition of 2.0 g/L Phytagel.

The leaf tissue was again blotted with sterile paper towels to remove remaining Agrobacteria and then transferred into callus induction medium (MS medium containing 2,4-D and kinetin; Sondahl and Sharp, 1977), containing 500 μg/mL carbenicillin, and either 100 to 300 μg/mL kanamycin monosulfate or 10 to 20 μg/mL geneticin (G418). After 13 days of culture at 25° C. in the dark, primary callus started to appear.

d) Subculturing of Coffee Leaf Callus Tissue Containing the pKRCACS-S, pKRCACO-S, pKRCACS-A or pKRCACO-A Plasmids The antibiotic resistant calli were subcultured monthly using embryo induction media M II (basal salts, halfstrength MS salts, 10 mg thiamine HCl, 40 mg cysteine HCl, 100 mg myo-inositol, 40 g sucrose, 2 mg BA, 1 mg pyridoxine, 1 mg nicotinic acid, 2.0 g phytagel, pH 5.65; Yasuda and Fujii, 1985) containing 300 µg/mL carbenicillin, and 150–200 µg/mL kanamycin for three months. These calli were then subcultured for thirty days into M II medium containing 100 µg/mL kanamycin, and for a further thirty days into M II medium containing 50 µg/mL kanamycin. Somatic embryos formed in this last medium. The somatic embryos developed into plantlets on germination media M III lacking growth regulators (basal salts, full-strength MS salts, 10 mg thiamine HCl, 40 mg cysteine HCl, 100 mg myo-inositol, 40 g sucrose, 2 g phytagel, pH 5.65; Sondahl and Sharp, 1977) under fluorescent light.

The foregoing examples are for illustrative purposes only, and should not be viewed as limiting the scope of applicants' invention, which is set forth in the claims appended hereto.

We claim:

1. A substantially pure nucleic acid that codes on expression for a coffee-fruit expressed ACC oxidase.

2. A coffee plant transformed with a nucleic acid sequence from a coffee fruit that codes on transcription for an RNA that is antisense to the mRNA that codes on expression for a coffee fruit-expressed ACC oxidase, wherein the RNA has a length sufficient to interfere with the expression of the coffee fruit-expressed ACC oxidase.

3. A coffee bean from the coffee plant of claim 2, wherein the coffee bean comprises said nucleic acid sequence.

4. A coffee plant transformed with a nucleic acid sequence from a coffee fruit that codes on transcription for an RNA that is sense to the mRNA that codes on expression for a coffee fruit-expressed ACC oxidase, wherein the RNA has a length sufficient to interfere with the expression of the coffee fruit-expressed ACC oxidase.

5. A coffee bean from the coffee plant of claim 4, wherein the coffee bean comprises said nucleic acid sequence.

6. A coffee plant transformed with a nucleic acid sequence that codes for an RNA that is sense or antisense to the mRNA that codes on expression for a coffee fruit-expressed ACC oxidase, wherein the nucleic acid sequence is linked to a transcription promoter in a sense or an antisense orientation in a transformation vector, wherein the coffee plant is transformed by the vector and the nucleic acid sequence is integrated into the genome of the coffee plant in the sense or the antisense orientation, and wherein the RNA has a length sufficient to interfere with the expression of the coffee fruit-expressed ACC oxidase.

7. A coffee bean from the coffee plant of claim 6, wherein the coffee bean comprises said nucleic acid sequence.

8. A coffee plant transformed with a nucleic acid sequence that codes on expression for a coffee fruit-expressed ACC oxidase.

9. The coffee plant of claim 8, wherein the nucleic-acid sequence is linked to a transcription promoter in an antisense orientation.

10. The coffee plant of claim 8, wherein the nucleic acid sequence is linked to a transcription promoter in a sense orientation.

11. A coffee bean from the coffee plant of claim 8, wherein the coffee bean comprises said nucleic acid sequence.

12. A transformed coffee plant produced by the process of inserting into the plant genome a nucleic acid sequence from a coffee fruit that codes on transcription for an RNA that is antisense to the mRNA that codes on expression for a coffee fruit-expressed ACC oxidase.

13. A transformed coffee plant produced by the process of inserting into the plant genome a nucleic acid sequence from a coffee fruit that codes on transcription for an RNA that is sense to the mRNA that codes on expression for a coffee fruit-expressed ACC oxidase.

14. A transforming vector comprising a transcription promoter operably linked to:
  (i) a nucleic acid sequence from a coffee fruit that codes on expression for a coffee fruit-expressed ACC oxidase; or
  (ii) a nucleic acid sequence from a coffee fruit that codes on transcription for an RNA that is sense or antisense to a coffee fruit-expressed mRNA for ACC oxidase, wherein the RNA has a length sufficient to interfere with the expression of a coffee fruit-expressed ACC oxidase.

15. The transforming vector of claim 14, wherein the nucleic acid sequence is operably linked to the transcription promoter in a sense orientation.

16. The transforming vector of claim 14, wherein the nucleic acid sequence is operably linked to the transcription promoter in an antisense orientation.

17. A coffee plant cell transformed with a nucleic acid sequence from a coffee fruit that codes on transcription for an RNA that is antisense to the mRNA that codes on expression for a coffee fruit-expressed ACC oxidase, wherein the RNA has a length sufficient to interfere with the expression of the coffee fruit-expressed ACC oxidase.

18. A coffee plant cell transformed with a nucleic acid sequence from a coffee fruit that codes on transcription for an RNA that is sense to the mRNA that codes on expression for a coffee fruit-expressed ACC oxidase wherein the RNA has a length sufficient to interfere with the expression of the coffee fruit-expressed ACC oxidase.

19. A coffee plant cell transformed with a nucleic acid sequence from a coffee fruit that codes for an RNA that is sense or antisense to the mRNA that codes on expression for a coffee fruit-expressed ACC oxidase, wherein the nucleic acid sequence is integrated into the genome of the coffee plant cell in a sense or an antisense orientation, and wherein the RNA has a length sufficient to interfere with the expression of the coffee fruit-expressed ACC oxidase.

20. A coffee plant cell transformed with a nucleic acid sequence that codes on expression for a coffee fruit-expressed ACC oxidase.

21. The coffee plant cell of claim 20, wherein the nucleic acid sequence is operably linked to a transcription promoter in an antisense orientation.

22. The coffee plant call of claim 20, wherein the nucleic acid sequence is operably linked to a transcription promoter in a sense orientation.

23. A transformed coffee plant cell produced by the process of inserting into the plant cell genome a nucleic acid sequence from a coffee fruit that codes on transcription for an RNA that is antisense to the mRNA that codes on expression for a coffee fruit-expressed ACC oxidase.

24. A transformed coffee plant cell produced by the process of inserting into the plant cell genome a nucleic acid sequence from a coffee fruit that codes on transcription for an RNA that is sense to the mRNA that codes on expression for a coffee fruit-expressed ACC oxidase.

25. A coffee plant regenerated from the transformed coffee plant cell of claim 18.

26. A coffee plant regenerated from the transformed coffee plant cell of claim 19.

27. A coffee plant regenerated from the transformed coffee plant cell of claim 20.

28. A coffee plant regenerated from the transformed coffee plant cell of claim 23.

29. A coffee plant regenerated from the transformed coffee plant cell of claim 24.

30. A method for transforming a coffee plant cell with a nucleic acid sequence from a coffee fruit that codes on transcription for an RNA that is antisense to the mRNA that codes for a coffee fruit-expressed ACC oxidase, comprising the steps of:
  providing a transforming vector comprising a nucleic acid sequence from a coffee fruit that codes on transcription for an RNA that is antisense to a coffee fruit-expressed mRNA for ACC oxidase, wherein the RNA has a length sufficient to interfere with the expression of a coffee fruit-expressed ACC oxidase, and wherein the nucleic acid is operably linked to a transcription promoter in an antisense orientation; and
  inserting the transforming vector into a coffee plant cell, wherein the nucleic acid sequence thereafter becomes inserted into the genome of the coffee plant cell.

31. A method for transforming a coffee plant cell with a nucleic acid sequence from a coffee fruit that codes on transcription for an RNA that is sense to the mRNA that codes for a coffee fruit-expressed ACC oxidase, comprising the steps of:
  providing a transforming vector comprising a nucleic acid sequence from a coffee fruit that codes on transcription for an RNA that is sense to a coffee fruit-expressed mRNA for ACC oxidase, wherein the RNA has a length sufficient to interfere with the expression of a coffee fruit-expressed ACC oxidase, wherein the nucleic acid is operably linked to a transcription promoter in a sense orientation; and
  inserting the transforming vector into a coffee plant cell, wherein the nucleic acid thereafter becomes inserted into the genome of the coffee plant cell.

32. A method for controlling the ripening of coffee fruit, comprising:
- (a) transforming a coffee plant cell with a transforming vector comprising a nucleic acid sequence from a coffee fruit that codes on transcription for an RNA that is sense or antisense to a coffee fruit-expressed mRNA for ACC oxidase, wherein the RNA has a length sufficient to interfere with the expression of a coffee fruit-expressed ACC oxidase, wherein the nucleic acid is operably linked to a transcription promoter in a sense or an antisense orientation;
- (b) growing a transformed coffee plant from the transformed coffee plant cell, wherein the coffee plant has a mature coffee fruit; and
- (c) applying exogenous ethylene to the transformed coffee plant to allow the mature coffee fruit to ripen.

* * * * *

SEQUENCE LISTING (1) GENERAL INFORMATION:

(iii) NUMBER OF SEQUENCES: 21

(2) INFORMATION FOR SEQ ID NO: 1:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: other nucleic acid
      (A) DESCRIPTION: primer (v) FRAGMENT TYPE: Internal fragment (xi) SEQUENCE DESCRIPTION: SEQ ID NO: 1:

GAGAGAGAGA GAGAGAGAGA ACTAGTCTCG AGTTTTTTTT TTTTTTTTTT      50

(2) INFORMATION FOR SEQ ID NO: 2:

(i) SEQUENCE CHARACTERISTICS:
      (A) LENGTH: 13 base pairs
      (B) TYPE: nucleic acid
      (D) TOPOLOGY: linear (ii) MOLECULE TYPE: other nucleic acid
      (A) DESCRIPTION: primer (v) FRAGMENT TYPE: Internal fragment (xi) SEQUENCE DESCRIPTION: SEQ ID NO: 2:

AATTCGGCAC GAG      13

(2) INFORMATION FOR SEQ ID NO: 3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: OTHER NUCLEIC ACID
      (A) DESCRIPTION: PRIMER (v) FRAGMENT TYPE: Internal (ix) FEATURE:
      (D) OTHER INFORMATION: R is G or A
          Y is T/U or C (xi) SEQUENCE DESCRIPTION: SEQ ID NO: 3:

GCCAAGCTTC CRTGRTARTC YTGRAA      26

(2) INFORMATION FOR SEQ ID NO: 4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: OTHER NUCLEAR ACID
            (A) DESCRIPTION: PRIMER (v) FRAGMENT TYPE: INTERNAL (ix) FEATURE:
            (D) OTHER INFORMATION:   R is G or A
                Y is T/U or C
                H is A or C or T/U (xi) SEQUENCE DESCRIPTION: SEQ ID NO: 4:

TTYCARGAYT AYCAYGGHYT                                                   20

(2) INFORMATION FOR SEQ ID NO: 5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: OTHER NUCLEIC ACID
            (A) DESCRIPTION: PRIMER (v) FRAGMENT TYPE: INTERNAL (ix) FEATURE:
            (D) OTHER INFORMATION:   H is A or C or T/U
                D is A or G or T/U
                R is G or A
                W is A or T/U
                Y is T/U or C
                N is A or C or G or T/U (xi) SEQUENCE DESCRIPTION: SEQ ID NO: 5:

CCHGGDARNC CYAWRTCTTT                                                   20

(2) INFORMATION FOR SEQ ID NO: 6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: OTHER NUCLEIC ACID
            (A) DESCRIPTION: PRIMER (v) FRAGMENT TYPE: INTERNAL (xi) SEQUENCE DESCRIPTION: SEQ ID NO: 6:

TAATACGACT CACTATAGGG                                                   20

(2) INFORMATION FOR SEQ ID NO: 7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: OTHER NUCLEIC ACID
            (A) DESCRIPTION: PRIMER (v) FRAGMENT TYPE: INTERNAL (xi) SEQUENCE DESCRIPTION: SEQ ID NO: 7:

AATTAACCCT CACTAAAGGG                                                          20

(2) INFORMATION FOR SEQ ID NO: 8:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: OTHER NUCLEIC ACID
            (A) DESCRIPTION: PRIMER (v) FRAGMENT TYPE: Internal (ix) FEATURE:
            (D) OTHER INFORMATION: N is inosine
                K is G or T/U
                R is G or A (xi) SEQUENCE DESCRIPTION: SEQ ID NO: 8:

TCATNGCKKC RAKNGGTTC                                                           19

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: OTHER NUCLEIC ACID
            (A) DESCRIPTION: PRIMER (v) FRAGMENT TYPE: Internal (xi) SEQUENCE DESCRIPTION: SEQ ID NO: 9:

GACACTGTGG AGAGGCTGAC                                                          20

(2) INFORMATION FOR SEQ ID NO: 10:

(i) SEQUENCE CHARACTERISTICS:
            (A) LENGTH: 488 amino acid residues
            (B) TYPE: amino acid
            (C) STRANDEDNESS: single
            (D) TOPOLOGY: linear (ii) MOLECULE TYPE: protein (ix) FEATURE:
            (A) NAME/KEY:CDS
            (B) LOCATION:178..1653

(xi) SEQUENCE DESCRIPTION: SEQ ID NO: 10:

Met Glu Phe Ser Leu Lys Asn Glu Gln Gln Gln Leu Leu Ser Lys
 1               5                  10                  15

Met Ala Thr Asn Asp Gly His Gly Glu Asn Ser Pro Tyr Phe Asp
                20                  25                  30

Gly Trp Lys Ala Tyr Asp Ser Asp Pro Tyr His Pro Thr Arg Asn
                35                  40                  45

Pro Asn Gly Val Ile Gln Met Gly Leu Ala Glu Asn Gln Leu Cys
                50                  55                  60

Phe Asp Leu Ile Glu Glu Trp Val Leu Asn Asn Pro Glu Ala Ser
                65                  70                  75

Ile Cys Thr Ala Glu Gly Ala Asn Lys Phe Met Glu Val Ala Ile
                80                  85                  90

```
Tyr Gln Asp Tyr His Gly Leu Pro Glu Phe Arg Asn Ala Val Ala
                 95                    100                 105

Arg Phe Met Glu Lys Val Arg Gly Asp Arg Val Lys Phe Asp Pro
                110                    115                 120

Asn Arg Ile Val Met Ser Gly Ala Thr Gly Ala His Glu Thr
                125                    130                 135

Leu Ala Phe Cys Leu Ala Asp Pro Glu Asp Ala Phe Leu Val Pro
                140                    145                 150

Thr Pro Tyr Tyr Pro Gly Phe Asp Arg Asp Leu Arg Trp Arg Thr
                155                    160                 165

Gly Met Gln Leu Leu Pro Ile Val Cys Arg Ser Ser Asn Asp Phe
                170                    175                 180

Lys Val Thr Lys Glu Ser Met Glu Ala Ala Tyr Gln Lys Ala Gln
                185                    190                 195

Glu Ala Asn Ile Arg Val Lys Gly Phe Leu Leu Asn Asn Pro Ser
                200                    205                 210

Asn Pro Leu Gly Thr Val Leu Asp Arg Glu Thr Leu Ile Asp Ile
                215                    220                 225

Val Thr Phe Ile Asn Asp Lys Asn Ile His Leu Ile Cys Asp Glu
                230                    235                 240

Ile Tyr Ser Ala Thr Val Phe Ser Gln Pro Glu Phe Ile Ser Ile
                245                    250                 255

Ser Glu Ile Ile Glu His Asp Val Gln Cys Asn Arg Asp Leu Ile
                260                    265                 270

His Leu Val Tyr Ser Leu Ser Lys Asp Leu Gly Phe Pro Gly Phe
                275                    280                 285

Arg Val Gly Ile Leu Tyr Ser Tyr Asn Asp Ala Val Val Ser Cys
                290                    295                 300

Ala Arg Lys Met Ser Ser Phe Gly Leu Val Ser Thr Gln Thr Gln
                305                    310                 315

His Leu Ile Ala Ser Met Leu Ser Asp Glu Ala Phe Met Asp Lys
                320                    325                 330

Ile Ile Ser Thr Ser Ser Glu Arg Leu Ala Ala Arg His Gly Leu
                335                    340                 345

Phe Thr Arg Gly Leu Ala Gln Val Gly Ile Gly Thr Leu Lys Ser
                350                    355                 360

Ser Ala Gly Leu Tyr Phe Trp Met Asp Leu Arg Arg Leu Leu Arg
                365                    370                 375

Glu Ser Thr Phe Glu Ala Glu Met Glu Leu Trp Arg Ile Ile Ile
                380                    385                 390

His Glu Val Lys Leu Asn Val Ser Pro Gly Leu Ser Phe His Cys
                395                    400                 405

Ser Glu Pro Gly Trp Phe Arg Val Cys Phe Ala Asn Met Asp Asp
                410                    415                 420

Glu Ser Val Arg Val Ala Leu Arg Arg Ile His Lys Phe Val Leu
                425                    430                 435

Val Gln Gly Lys Ala Thr Glu Pro Thr Thr Pro Lys Ser Arg Cys
                440                    445                 450

Gly Ser Ser Lys Leu Gln Leu Ser Leu Ser Phe Arg Arg Leu Asp
                455                    460                 465

Glu Arg Val Met Gly Ser His Met Met Ser Pro His Ser Pro Met
                470                    475                 480
```

Ala Ser Pro Leu Val Arg Ala Thr
            485

(2) INFORMATION FOR SEQ ID NO: 11:

(i) SEQUENCE CHARACTERISTICS:
        (A) LENGTH: 2040 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY:CDS
        (B) LOCATION:178..1653

(xi) SEQUENCE DESCRIPTION: SEQ ID NO: 11:

```
GTAATCTCTT CTAAAATCAA CCATTCTCTT CATTCTTCAC TTGACAAGGC            50

CACTGCATTC TTCATTCTTT CTTGATATAT AGCCATTTTT TCATTCTTT            100

CTTGATATAT AGCCATTTTT TCATTCTTT CTTCATTCAT TGTCTGGAGA            150

AGTTGGTTGA GTTTTCTTGA AAATTCAAGC AAAACA ATG GAG TTC AGT            198
                                        Met Glu Phe Ser
                                         1

TTG AAA AAC GAA CAA CAA CAA CTC TTG TCG AAG ATG GCA ACC            240
Leu Lys Asn Glu Gln Gln Gln Leu Leu Ser Lys Met Ala Thr
  5              10                  15

AAC GAT GGA CAT GGC GAA AAC TCG CCT TAT TTT GAT GGT TGG            282
Asn Asp Gly His Gly Glu Asn Ser Pro Tyr Phe Asp Gly Trp
 20                  25                  30

AAG GCA TAT GAT AGT GAT CCT TAC CAT CCC ACC AGA AAT CCT            324
Lys Ala Tyr Asp Ser Asp Pro Tyr His Pro Thr Arg Asn Pro
         35                  40                  45

AAT GGT GTT ATA CAG ATG GGA CTC GCA GAA AAT CAG TTA TGC            366
Asn Gly Val Ile Gln Met Gly Leu Ala Glu Asn Gln Leu Cys
                 50                  55                  60

TTT GAT TTG ATC GAG GAA TGG GTT CTG AAC AAT CCA GAG GCT            408
Phe Asp Leu Ile Glu Glu Trp Val Leu Asn Asn Pro Glu Ala
                     65                  70

TCC ATT TGC ACA GCA GAA GGA GCG AAC AAA TTC ATG GAA GTT            450
Ser Ile Cys Thr Ala Glu Gly Ala Asn Lys Phe Met Glu Val
 75                  80                  85

GCT ATC TAT CAA GAT TAT CAT GGC TTG CCA GAG TTC AGA AAT            492
Ala Ile Tyr Gln Asp Tyr His Gly Leu Pro Glu Phe Arg Asn
         90                  95                 100

GCT GTA GCA AGG TTC ATG GAG AAG GTG AGA GGT GAC AGA GTC            534
Ala Val Ala Arg Phe Met Glu Lys Val Arg Gly Asp Arg Val
                105                 110                 115

AAG TTC GAT CCC AAC CGC ATT GTG ATG AGT GGT GGG GCA ACC            576
Lys Phe Asp Pro Asn Arg Ile Val Met Ser Gly Gly Ala Thr
                    120                 125                 130

GGA GCT CAT GAA ACT CTG GCC TTC TGT TTA GCT GAC CCT GAA            618
Gly Ala His Glu Thr Leu Ala Phe Cys Leu Ala Asp Pro Glu
                135                 140

GAT GCG TTT TTG GTA CCC ACA CCA TAT TAT CCA GGA TTT GAT            660
Asp Ala Phe Leu Val Pro Thr Pro Tyr Tyr Pro Gly Phe Asp
145                 150                 155

CGG GAT TTG AGG TGG CGA ACA GGG ATG CAA CTT CTT CCA ATT            702
Arg Asp Leu Arg Trp Arg Thr Gly Met Gln Leu Leu Pro Ile
            160                 165                 170

GTT TGT CGC AGC TCC AAT GAT TTT AAG GTC ACT AAA GAA TCC            744
```

```
                                                                    -continued Val Cys Arg Ser Ser Asn Asp Phe Lys Val Thr Lys Glu Ser
        175                 180                 185

ATG GAA GCT GCT TAT CAG AAA GCT CAA GAA GCC AAC ATC AGA             786
Met Glu Ala Ala Tyr Gln Lys Ala Gln Glu Ala Asn Ile Arg
            190                 195                 200

GTA AAG GGG TTC CTC TTA AAT AAT CCA TCA AAT CCA TTG GGA             828
Val Lys Gly Phe Leu Leu Asn Asn Pro Ser Asn Pro Leu Gly
                    205                 210

ACT GTT CTT GAC AGG GAA ACT TTG ATT GAT ATA GTC ACA TTC             870
Thr Val Leu Asp Arg Glu Thr Leu Ile Asp Ile Val Thr Phe
215                 220                 225

ATC AAT GAC AAA AAT ATC CAC TTG ATT TGT GAT GAG ATA TAT             912
Ile Asn Asp Lys Asn Ile His Leu Ile Cys Asp Glu Ile Tyr
        230                 235                 240

TCT GCC ACC GTC TTC AGC CAG CCC GAA TTC ATC AGC ATC TCT             954
Ser Ala Thr Val Phe Ser Gln Pro Glu Phe Ile Ser Ile Ser
            245                 250                 255

GAA ATA ATT GAG CAT GAT GTT CAA TGC AAC CGT GAT CTC ATA             996
Glu Ile Ile Glu His Asp Val Gln Cys Asn Arg Asp Leu Ile
                    260                 265                 270

CAT CTT GTG TAT AGC CTG TCC AAG GAC TTG GGC TTC CCT GGA             1038
His Leu Val Tyr Ser Leu Ser Lys Asp Leu Gly Phe Pro Gly
                275                 280

TTC AGA GTT GGC ATT TTG TAT TCA TAT AAT GAC GCT GTT GTC             1080
Phe Arg Val Gly Ile Leu Tyr Ser Tyr Asn Asp Ala Val Val
285                 290                 295

AGC TGT GCT AGA AAA ATG TCG AGT TTC GGC CTT GTT TCA ACA             1122
Ser Cys Ala Arg Lys Met Ser Ser Phe Gly Leu Val Ser Thr
        300                 305                 310

CAA ACT CAG CAT CTG ATT GCA TCA ATG TTA TCG GAC GAA GCA             1164
Gln Thr Gln His Leu Ile Ala Ser Met Leu Ser Asp Glu Ala
            315                 320                 325

TTT ATG GAC AAA ATC ATT TCC ACG AGC TCA GAG AGA TTA GCT             1206
Phe Met Asp Lys Ile Ile Ser Thr Ser Ser Glu Arg Leu Ala
                    330                 335                 340

GCA AGG CAT GGT CTT TTC ACA AGA GGA CTT GCT CAA GTA GGC             1248
Ala Arg His Gly Leu Phe Thr Arg Gly Leu Ala Gln Val Gly
                345                 350

ATT GGC ACC TTA AAA AGC AGT GCG GGC CTT TAT TTC TGG ATG             1290
Ile Gly Thr Leu Lys Ser Ser Ala Gly Leu Tyr Phe Trp Met
355                 360                 365

GAC TTA AGG AGA CTC CTC AGG GAG TCC ACA TTT GAG GCA GAA             1332
Asp Leu Arg Arg Leu Leu Arg Glu Ser Thr Phe Glu Ala Glu
        370                 375                 380

ATG GAA CTT TGG AGG ATC ATA ATA CAT GAA GTC AAG CTC AAT             1374
Met Glu Leu Trp Arg Ile Ile Ile His Glu Val Lys Leu Asn
            385                 390                 395

GTT TCA CCA GGC TTA TCT TTC CAT TGC TCA GAA CCA GGA TGG             1416
Val Ser Pro Gly Leu Ser Phe His Cys Ser Glu Pro Gly Trp
                    400                 405                 410

TTC AGA GTT TGC TTT GCC AAC ATG GAC GAC GAA AGT GTG AGA             1458
Phe Arg Val Cys Phe Ala Asn Met Asp Asp Glu Ser Val Arg
                415                 420

GTT GCT CTC AGA AGA ATC CAC AAA TTT GTG CTT GTT CAG GGC             1500
Val Ala Leu Arg Arg Ile His Lys Phe Val Leu Val Gln Gly
425                 430                 435

AAG GCA ACA GAG CCA ACA ACT CCA AAG AGT CGC TGC GGA AGC             1542
Lys Ala Thr Glu Pro Thr Thr Pro Lys Ser Arg Cys Gly Ser
        440                 445                 450
```

```
AGC AAA CTT CAA CTC AGC TTA TCT TTC CGC AGA TTG GAC GAA        1584
Ser Lys Leu Gln Leu Ser Leu Ser Phe Arg Arg Leu Asp Glu
        455                 460                 465

AGG GTG ATG GGA TCG CAT ATG ATG TCC CCT CAC TCC CCG ATG        1626
Arg Val Met Gly Ser His Met Met Ser Pro His Ser Pro Met
            470                 475                 480

GCT TCA CCT TTG GTT CGG GCT ACA TAAATCATTT CTTGATCAGA          1670
Ala Ser Pro Leu Val Arg Ala Thr
                485

TCATATAGCA AAGATTCCTG AGTAAATACT CGAAACCCTT TCTGGATAAC         1720

TGAAAAGAGA GTTGTTGATT CTTTGCTGTA TCATACAAAC ACGTTACAGG         1770

CATTTTTTGG CCATCTGATG CGTGCAAATT GCATCAAATG CTTTTATTAT         1820

TGTCATATTC ATTTGTGTAC CTTGGTTTTC CTTGCCCTTC AGTCCTCCTT         1870

GTTTTTTGTT TCTTTGTTAT TATTTTCTTC CAGTTGATCA GTTAAACGAA         1920

GGAAGCTCAA TTGTTTCAAG CTATTAGTAA CAGATCATTT TGTAATAGCA         1970

ATAGTTCAG GATTCTGAAA TGAAAGTTTA TCATTTTTCC ATCATTTTAA          2020

AAAAAAAAAA AAAAAAAAA                                           2040
```

(2) INFORMATION FOR SEQ ID NO: 12:

(i) SEQUENCE CHARACTERISTICS:
        (A) LENGTH: 318 amino acid residues
        (B) TYPE: amino acid
        (C) STRANDEDNESS: single
        (D) TOPOLOGY: linear (ii) MOLECULE TYPE: protein (ix) FEATURE:
        (A) NAME/KEY:CDS
        (B) LOCATION:46..1003

(xi) SEQUENCE DESCRIPTION: SEQ ID NO: 12

```
Met Ala Thr Phe Pro Leu Ile Asp Met Glu Lys Leu Asp Gly Glu
 1               5                  10                  15

Glu Arg Ala Ala Thr Met Gly Val Ile Lys Asp Ala Cys Glu Ser
                20                  25                  30

Trp Gly Phe Phe Glu Val Leu Asn His Gly Ile Ser Asn Glu Leu
                35                  40                  45

Met Asp Thr Val Glu Arg Leu Thr Lys Glu His Tyr Lys Lys Cys
                50                  55                  60

Met Glu Leu Lys Phe Lys Glu Met Val Glu Ser Lys Glu Leu Glu
                65                  70                  75

Ala Val Gln Thr Glu Ile Asn Asp Leu Asp Trp Glu Ser Thr Phe
                80                  85                  90

Phe Leu Arg His Leu Pro Val Ser Asn Ile Ser Glu Val Pro Asp
                95                 100                 105

Leu Asp Asp Glu Tyr Arg Lys Val Met Lys Glu Phe Ala Leu Gln
               110                 115                 120

Leu Glu Lys Leu Ala Glu Leu Leu Asp Leu Leu Cys Glu Asn
               125                 130                 135

Leu Gly Leu Glu Lys Gly Tyr Leu Lys Lys Ala Phe Tyr Gly Thr
               140                 145                 150

Lys Gly Pro Thr Phe Gly Thr Lys Val Ser Asn Tyr Pro Pro Cys
               155                 160                 165

Pro Arg Pro Glu Leu Ile Lys Gly Leu Arg Ala His Thr Asp Ala
```

-continued

```
                        170                 175                 180
Gly Gly Ile Ile Leu Leu Phe Gln Asp Asp Lys Val Ser Gly Leu
                185                 190                 195
Gln Leu Leu Lys Asp Gly Glu Trp Val Asp Val Pro Pro Met Arg
                200                 205                 210
His Ser Ile Val Ile Asn Ile Gly Asp Gln Leu Glu Val Ile Thr
                215                 220                 225
Asn Gly Lys Tyr Lys Ser Val Met His Arg Val Ile Ala Gln Pro
                230                 235                 240
Asp Gly Asn Arg Met Ser Leu Ala Ser Phe Tyr Asn Pro Gly Ser
                245                 250                 255
Asp Ala Val Ile Tyr Pro Ala Pro Ala Leu Val Glu Lys Glu Ala
                260                 265                 270
Glu Asp Lys Gln Ile Tyr Pro Lys Phe Val Phe Glu Asp Tyr Met
                275                 280                 285
Lys Leu Tyr Ala Gly Leu Lys Phe Gln Ala Lys Glu Pro Arg Phe
                290                 295                 300
Glu Ala Met Lys Ala Val Glu Ser Thr Val Asn Leu Gly Pro Ile
                305                 310                 315
Ala Thr Val
        318
```

(2) INFORMATION FOR SEQ ID NO: 13:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: cDNA to mRNA (ix) FEATURE:
        (A) NAME/KEY:CDS
        (B) LOCATION:46..1003

(xi) SEQUENCE DESCRIPTION: SEQ ID NO: 13:

```
TGTAAACGAA GCATAAGCAC AAGCAAACAC AAACTAGAAA GAGAG ATG                        48
                                                   Met
                                                     1

GCT ACA TTC CCC CTA ATC GAC ATG GAG AAG CTT GAC GGT GAA                      90
Ala Thr Phe Pro Leu Ile Asp Met Glu Lys Leu Asp Gly Glu
         5                  10                  15

GAG AGG GCT GCC ACT ATG GGA GTC ATA AAA GAT GCT TGT GAA                     132
Glu Arg Ala Ala Thr Met Gly Val Ile Lys Asp Ala Cys Glu
             20                  25

AGC TGG GGC TTC TTT GAG GTG TTG AAT CAT GGG ATA TCT AAT                     174
Ser Trp Gly Phe Phe Glu Val Leu Asn His Gly Ile Ser Asn
 30                  35                  40

GAG CTC ATG GAC ACA GTG GAG AGG CTA ACA AAG GAG CAT TAC                     216
Glu Leu Met Asp Thr Val Glu Arg Leu Thr Lys Glu His Tyr
     45                  50                  55

AAG AAA TGT ATG GAA CTA AAG TTC AAG GAA ATG GTG GAG AGC                     258
Lys Lys Cys Met Glu Leu Lys Phe Lys Glu Met Val Glu Ser
         60                  65                  70

AAG GAA TTG GAA GCT GTT CAG ACT GAG ATC AAT GAT TTG GAC                     300
Lys Glu Leu Glu Ala Val Gln Thr Glu Ile Asn Asp Leu Asp
             75                  80                  85

TGG GAA AGT ACC TTC TTC TTG CGC CAT CTT CCT GTT TCC AAC                     342
Trp Glu Ser Thr Phe Phe Leu Arg His Leu Pro Val Ser Asn
```

|  |  |
|---|---|
| ATC TCA GAA GTC CCT GAT CTT GAT GAT GAA TAC AGA AAG GTT<br>Ile Ser Glu Val Pro Asp Leu Asp Asp Glu Tyr Arg Lys Val<br>100                        105                       110 | 384 |
| ATG AAG GAA TTT GCG TTG CAA CTT GAG AAA CTA GCA GAG CTC<br>Met Lys Glu Phe Ala Leu Gln Leu Glu Lys Leu Ala Glu Leu<br>115                       120                     125 | 426 |
| CTG TTG GAC TTG CTA TGC GAG AAC CTT GGC CTA GAG AAA GGC<br>Leu Leu Asp Leu Leu Cys Glu Asn Leu Gly Leu Glu Lys Gly<br>       130                   135                  140 | 468 |
| TAT CTG AAG AAA GCC TTC TAT GGC ACC AAA GGA CCA ACC TTT<br>Tyr Leu Lys Lys Ala Phe Tyr Gly Thr Lys Gly Pro Thr Phe<br>          145                  150               155 | 510 |
| GGC ACC AAA GTC AGC AAT TAC CCT CCA TGC CCT CGT CCA GAA<br>Gly Thr Lys Val Ser Asn Tyr Pro Pro Cys Pro Arg Pro Glu<br>                 160                  165 | 552 |
| CTG ATC AAG GGC CTC CGG GCA CAC ACC GAT GCC GGC GGC ATC<br>Leu Ile Lys Gly Leu Arg Ala His Thr Asp Ala Gly Gly Ile<br>170                       175                  180 | 594 |
| ATC CTG CTG TTC CAG GAT GAC AAG GTC AGC GGT CTC CAG CTC<br>Ile Leu Leu Phe Gln Asp Asp Lys Val Ser Gly Leu Gln Leu<br>         185                  190               195 | 636 |
| CTC AAG GAT GGT GAA TGG GTG GAT GTT CCG CCT ATG CGC CAC<br>Leu Lys Asp Gly Glu Trp Val Asp Val Pro Pro Met Arg His<br>            200                  205             210 | 678 |
| TCC ATT GTA ATC AAC ATC GGC GAC CAA CTT GAG GTA ATC ACA<br>Ser Ile Val Ile Asn Ile Gly Asp Gln Leu Glu Val Ile Thr<br>               215                  220             225 | 720 |
| AAT GGA AAA TAC AAG AGT GTG ATG CAC CGG GTG ATA GCT CAA<br>Asn Gly Lys Tyr Lys Ser Val Met His Arg Val Ile Ala Gln<br>                   230                  235 | 762 |
| CCA GAT GGG AAC AGA ATG TCA CTA GCA TCA TTC TAC AAT CCA<br>Pro Asp Gly Asn Arg Met Ser Leu Ala Ser Phe Tyr Asn Pro<br>240                       245                    250 | 804 |
| GGA AGT GAT GCA GTG ATC TAT CCA GCA CCG GCA TTG GTT GAG<br>Gly Ser Asp Ala Val Ile Tyr Pro Ala Pro Ala Leu Val Glu<br>       255                   260                  265 | 846 |
| AAA GAG GCA GAG GAC AAG CAG ATA TAT CCC AAG TTT GTG TTC<br>Lys Glu Ala Glu Asp Lys Gln Ile Tyr Pro Lys Phe Val Phe<br>               270                  275             280 | 888 |
| GAG GAC TAC ATG AAG CTC TAT GCT GGC CTT AAG TTC CAA GCT<br>Glu Asp Tyr Met Lys Leu Tyr Ala Gly Leu Lys Phe Gln Ala<br>                 285                  290             295 | 930 |
| AAA GAG CCC AGG TTT GAA GCC ATG AAG GCC GTG GAA AGC ACC<br>Lys Glu Pro Arg Phe Glu Ala Met Lys Ala Val Glu Ser Thr<br>                   300                  305 | 972 |
| GTA AAC TTG GGT CCA ATC GCA ACT GTT TGAGATAATA CACGCTTTGA<br>Val Asn Leu Gly Pro Ile Ala Thr Val<br>310                       315 | 1019 |
| TCTGCTGCTG TCTTATAATG CGCGTTTGCG TAATCATATC CTAGCATAGT | 1069 |
| ATATCTGAGA TCTGAGTCTG TATTGTGGTG TGAGTTTGGT TTAGCCCCTT | 1119 |
| GTTAATGCTT GGATTGGACT AGTTAAATGT GGAGCTGGTT TGTTAGATAA | 1169 |
| GATAGTCTTG CCAGGATCTT TGAGTAAATA TGATTCTGCG GAAGTCTGCG | 1219 |
| GTGAATGATA ACGTGTAAAG CAATCCGAAA GTTACCTTTC TGGGGCTTTG | 1269 |
| TCATATGCAA TGGAGAAGGA ATCTTCCAAA AAAAAAAAA AAAAAAAAA | 1319 |
| A | 1320 |

(2) INFORMATION FOR SEQ ID NO: 14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: loxA synthetic oligonucleotide (v) FRAGMENT TYPE: Internal fragment (xi) SEQUENCE DESCRIPTION: SEQ ID NO: 14:

```
AGCTATAACT TCGTATAGCA TACATTATAC GAAGTTAT                              38
```

(2) INFORMATION FOR SEQ ID NO: 15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: loxB synthetic oligonucleotide (v) FRAGMENT TYPE: Internal fragment (xi) SEQUENCE DESCRIPTION: SEQ ID NO: 15:

```
AGCTATAACT TCGTATAATG TATGCTATAC GAAGTTAT                              38
```

(2) INFORMATION FOR SEQ ID NO: 16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: loxC synthetic oligonucleotide (v) FRAGMENT TYPE: Internal fragment (xi) SEQUENCE DESCRIPTION: SEQ ID NO: 16:

```
ATAACTTCGT ATAGCATACA TTATACGAAG TTATAGCT                              38
```

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: primer (v) FRAGMENT TYPE: Internal fragment (xi) SEQUENCE DESCRIPTION: SEQ ID NO: 17:

```
CCA CTA TCC TTC GCA AGA CC                                            20
```

(2) INFORMATION FOR SEQ ID NO: 18:

(i) SEQUENCE CHARACTERISTICS:
        (A) LENGTH: 20 base pairs
        (B) TYPE: nucleic acid

```
            (C) STRANDEDNESS: single
            (D) TOPOLOGY: linear (ii) MOLECULE TYPE: other nucleic acid
            (A) DESCRIPTION: primer (v) FRAGMENT TYPE: Internal fragment (xi) SEQUENCE DESCRIPTION: SEQ ID NO: 18:

TTG CCA TCT TCG ACA AGA CT                                                  20

(2) INFORMATION FOR SEQ ID NO: 19:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: primer (v) FRAGMENT TYPE: Internal fragment (xi) SEQUENCE DESCRIPTION: SEQ ID NO: 19:

CTG TTG TCA GCT GTG CTA                                                     18

(2) INFORMATION FOR SEQ ID NO: 20:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: primer (v) FRAGMENT TYPE: Internal fragment (xi) SEQUENCE DESCRIPTION: SEQ ID NO: 20:

GGA CTT CTG AGA TGT TGG AA                                                  20

(2) INFORMATION FOR SEQ ID NO: 21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: primer (v) FRAGMENT TYPE: Internal fragment (xi) SEQUENCE DESCRIPTION: SEQ ID NO: 21:

TGG TGG AGA GCA AGG AAT TG                                                  20
```